(12) United States Patent
Wong et al.

(10) Patent No.: US 7,696,152 B2
(45) Date of Patent: Apr. 13, 2010

(54) BIOLOGICALLY ACTIVE PEPTIDE CONSISTING OF TYROSYL-SERYL-LEUCINE (YSL)

(75) Inventors: Wai Ming Wong, Hong Kong (CN); Kong Lam, Shenzhen (CN)

(73) Assignee: CMS Peptides Patent Holdings Company Limited, Tortola (VG)

( * ) Notice: Subject to any disclaimer, the term of this patent is extended or adjusted under 35 U.S.C. 154(b) by 754 days.

(21) Appl. No.: 11/460,998

(22) Filed: Jul. 31, 2006

(65) Prior Publication Data

US 2008/0233136 A1   Sep. 25, 2008

Related U.S. Application Data

(60) Division of application No. 10/237,405, filed on Sep. 5, 2002, now Pat. No. 7,491,689, which is a continuation-in-part of application No. 10/178,684, filed on Jun. 20, 2002, now abandoned, which is a continuation-in-part of application No. 09/904,492, filed on Jul. 13, 2001, now abandoned.

(51) Int. Cl.
   *A61K 38/00*   (2006.01)
(52) U.S. Cl. .................... 514/2; 424/185.1; 530/331
(58) Field of Classification Search .................... None
   See application file for complete search history.

(56) References Cited

U.S. PATENT DOCUMENTS

| 5,556,744 A | 9/1996 | Weiner | |
|---|---|---|---|
| 5,760,000 A * | 6/1998 | Habibi | 514/15 |
| 2004/0043438 A1* | 3/2004 | Holm et al. | 435/7.92 |

FOREIGN PATENT DOCUMENTS

| EP | 257406 B2 | 3/1988 |
| EP | 382012 B1 | 8/1990 |
| FR | 2794370 A1 | 12/2000 |
| WO | 9109613 A1 | 7/1991 |
| WO | 9618646 A3 | 6/1996 |
| WO | WO98/59071 A1 | 12/1998 |
| WO | WO00/12762 A1 | 3/2000 |
| WO | WO01/29228 A1 | 4/2001 |

OTHER PUBLICATIONS

Ram et al., Ann. N.Y. Acad. Sci., 2007, 1110:410-425.*

Owens et al., "Structure-activity relationship of the neurotransmitter alpha-bag cell peptide on Aplysia LUQ neurons: implications regarding its inactivation in the extracellular space" (1992) Journal of Neurobiology, 23:656-670.*
Moisan et all, (1998). Structural Requirements and mechanism of the Pressor Activity of Leu-Val-Val-hemorphin-7, a Fragment of Hemoglobin B-chain n Rats. Peptides. 19(1) p. 119-131: Printed in USA.
Katoh et al, (1996). Mapping Myosin-Binding Sites on Actin Probed by Peptides that Inhibit Actomyosin Interaction. J. Biochem. 120, p. 580-586.
Hastings et al., (1982). cDNA clone analysis of six co-regulated mRNAs encoding skeletal muscle contractile proteins. Proc. Natl. Acad. Sci. USA vol. 79 p. 1553-1557.
Hietter et al., (1989). Isolation and structure of two novel 6-kDa dimeric peptides from the corpora cardiaca of the insect Locusta migratoria. Eur. J. Biochem. 182, p. 77-84.
Mezo et al., (1989). The Influence of the Side-Chain Sequence on the Structure-Activity Correlations of Immunomodulatory Branched Polypeptides. Synthesis and Conformational Analysis of New Model Polypeptides. Biopolymers, vol. 28, p. 1801-1826.
Westermann et al., (1990). Synthetic peptides identify the minimal substrate requirements of tubulin polyglutamylase in side chain elongation. FEBS Letters 459, p. 90-94.
Firtel et al., (1979). Unusual nucleotide sequences at the 5' end of actin genes in Dictyostelium discoideum. Proc. Natl. Acad. Sci. USA, vol. 76, No. 12, p. 6206-6210.
Genbank AAF04121. http://www.ncbi.nlm.nih.gov/entrez/viewer.fcgi?db=protein&val=6118500, Oct. 26, 1999.
Pati et al., Inhibition of Human Hepatocarcinoma Cell Proliferation by Mammalian and Fish Gonadotropin-Releasing Hormones, Endocrinology, vol. 136(1):75-84, 1995.
Sherwood et al., Primary structure of gonadotropin-releasing hormone from lamprey brain, J. Biol. Chem., 1986, 261 (11):4812-4819.
Ivanov et al. , Hemoglobin as a source of endogenous bioactive peptides: the concept of tissue-specific peptide pool, Biopolymers. 1997, 43:171-188.
Ding et al., The synthesis, distribution, and anti-hepatic cancer activity of YSL, Bioorganic & Medicinal Chemistry, 2004, 12:4989-4994.
Lai et al., Solid-State Chemical Stability of Proteins and Peptides, Journal of Pharmaceutical Sciences, 1999, 88 (5):489-500.
The amino acid masses, http://haven.isb-sib.ch/tools/isotopident/htdocs/aa-list.html, downloaded Apr. 5, 2006.

\* cited by examiner

*Primary Examiner*—Michael Szperka
(74) *Attorney, Agent, or Firm*—Eagle IP Limited; Jacqueline C. Lui

(57) ABSTRACT

A substantially pure and biologically active peptides consisting of tyrosyl-seryl-leucine (YSL) is disclosed. Nucleic acids that have sequences coding for the biologically active peptide and pharmaceutical formulation produced therefrom are also disclosed.

7 Claims, No Drawings

SEQUENCE LISTING

<160> NUMBER OF SEQ ID NOS: 30

<210> SEQ ID NO 1
<211> LENGTH: 10
<212> TYPE: PRT
<213> ORGANISM: Sus scrofa

<400> SEQUENCE: 1

Pro Thr Thr Lys Thr Tyr Phe Pro His Phe
1               5                   10

<210> SEQ ID NO 2
<211> LENGTH: 9
<212> TYPE: PRT
<213> ORGANISM: Sus scrofa

<400> SEQUENCE: 2

Val Val Tyr Pro Trp Thr Gln Arg Phe
1               5

<210> SEQ ID NO 3
<211> LENGTH: 13
<212> TYPE: PRT
<213> ORGANISM: Sus scrofa

<400> SEQUENCE: 3

Lys Ala Val Gly His Leu Asp Asp Leu Pro Gly Ala Leu
1               5                   10

<210> SEQ ID NO 4
<211> LENGTH: 18
<212> TYPE: PRT
<213> ORGANISM: Sus scrofa

<400> SEQUENCE: 4

Val Ala Pro Glu Glu His Pro Thr Leu Leu Thr Glu Ala Pro Leu Asn
1               5                   10                  15

Pro Lys

<210> SEQ ID NO 5
<211> LENGTH: 13
<212> TYPE: PRT
<213> ORGANISM: Sus scrofa

```
<400> SEQUENCE: 5

Leu Gly Met Glu Ala Cys Gly Ile His Glu Thr Thr Tyr
 1               5                  10

<210> SEQ ID NO 6
<211> LENGTH: 11
<212> TYPE: PRT
<213> ORGANISM: Sus scrofa

<400> SEQUENCE: 6

Leu Arg Val Ala Pro Glu Glu His Pro Val Leu
 1               5                  10

<210> SEQ ID NO 7
<211> LENGTH: 12
<212> TYPE: PRT
<213> ORGANISM: Sus scrofa

<400> SEQUENCE: 7

Ala Ala His His Pro Asp Asp Phe Asn Pro Ser Val
 1               5                  10

<210> SEQ ID NO 8
<211> LENGTH: 13
<212> TYPE: PRT
<213> ORGANISM: Sus scrofa

<400> SEQUENCE: 8

Pro Ser Ile Val Gly Arg Pro Arg His Gln Gly Val Met
 1               5                  10

<210> SEQ ID NO 9
<211> LENGTH: 13
<212> TYPE: PRT
<213> ORGANISM: Sus scrofa

<400> SEQUENCE: 9

Ile Gly Met Glu Ser Ala Gly Ile His Glu Thr Thr Tyr
 1               5                  10

<210> SEQ ID NO 10
<211> LENGTH: 9
<212> TYPE: PRT
<213> ORGANISM: Sus scrofa

<400> SEQUENCE: 10

Val Gly Met Gly Glu Lys Asp Ser Tyr
 1               5

<210> SEQ ID NO 11
<211> LENGTH: 9
<212> TYPE: PRT
<213> ORGANISM: Sus scrofa

<400> SEQUENCE: 11

Val Gly Met Gly Gln Lys Asp Ser Tyr
 1               5

<210> SEQ ID NO 12
<211> LENGTH: 10
<212> TYPE: PRT
<213> ORGANISM: Sus scrofa
```

```
<400> SEQUENCE: 12

Val Gly Met Gly Gln Lys Asp Ser Tyr Val
1               5                   10

<210> SEQ ID NO 13
<211> LENGTH: 10
<212> TYPE: PRT
<213> ORGANISM: Sus scrofa

<400> SEQUENCE: 13

Met Ala Thr Ala Ala Ser Ser Ser Ser Leu
1               5                   10

<210> SEQ ID NO 14
<211> LENGTH: 3
<212> TYPE: PRT
<213> ORGANISM: Sus scrofa

<400> SEQUENCE: 14

Tyr Ser Phe
1

<210> SEQ ID NO 15
<211> LENGTH: 3
<212> TYPE: PRT
<213> ORGANISM: Sus scrofa

<400> SEQUENCE: 15

Ala Ala Phe
1

<210> SEQ ID NO 16
<211> LENGTH: 3
<212> TYPE: PRT
<213> ORGANISM: Sus scrofa

<400> SEQUENCE: 16

Tyr Ser Leu
1

<210> SEQ ID NO 17
<211> LENGTH: 7
<212> TYPE: PRT
<213> ORGANISM: Sus scrofa

<400> SEQUENCE: 17

Thr Thr Tyr Asn Ser Ile Met
1               5

<210> SEQ ID NO 18
<211> LENGTH: 5
<212> TYPE: PRT
<213> ORGANISM: Sus scrofa

<400> SEQUENCE: 18

Phe Glu Glu Asn Met
1               5

<210> SEQ ID NO 19
<211> LENGTH: 5
<212> TYPE: PRT
<213> ORGANISM: Sus scrofa
```

```
<400> SEQUENCE: 19

Phe Glu Pro Ser Phe
1               5

<210> SEQ ID NO 20
<211> LENGTH: 4
<212> TYPE: PRT
<213> ORGANISM: Sus scrofa

<400> SEQUENCE: 20

Phe Asn Glu Glu
1

<210> SEQ ID NO 21
<211> LENGTH: 4
<212> TYPE: PRT
<213> ORGANISM: Sus scrofa

<400> SEQUENCE: 21

Phe Glu Glu Met
1

<210> SEQ ID NO 22
<211> LENGTH: 4
<212> TYPE: PRT
<213> ORGANISM: Sus scrofa

<400> SEQUENCE: 22

Phe Glu Glu Glu
1

<210> SEQ ID NO 23
<211> LENGTH: 4
<212> TYPE: PRT
<213> ORGANISM: Sus scrofa

<400> SEQUENCE: 23

Phe Glu Ser Phe
1

<210> SEQ ID NO 24
<211> LENGTH: 4
<212> TYPE: PRT
<213> ORGANISM: Sus scrofa

<400> SEQUENCE: 24

Pro Glu Asn Phe
1

<210> SEQ ID NO 25
<211> LENGTH: 4
<212> TYPE: PRT
<213> ORGANISM: Sus scrofa

<400> SEQUENCE: 25

Phe Val Asn Asp
1

<210> SEQ ID NO 26
<211> LENGTH: 5
<212> TYPE: PRT
<213> ORGANISM: Sus scrofa
```

```
-continued

<400> SEQUENCE: 26

Phe Gln Pro Ser Phe
1               5

<210> SEQ ID NO 27
<211> LENGTH: 6
<212> TYPE: PRT
<213> ORGANISM: Sus scrofa

<400> SEQUENCE: 27

Phe Asn Phe Val Pro Pro
1               5

<210> SEQ ID NO 28
<211> LENGTH: 10
<212> TYPE: PRT
<213> ORGANISM: Sus scrofa

<400> SEQUENCE: 28

Ala Gly Asp Asp Ala Pro Arg Ala Val Phe
1               5                   10

<210> SEQ ID NO 29
<211> LENGTH: 11
<212> TYPE: PRT
<213> ORGANISM: Sus scrofa

<400> SEQUENCE: 29

Leu Arg Val Ala Pro Glu Glu His Pro Thr Leu
1               5                   10

<210> SEQ ID NO 30
<211> LENGTH: 10
<212> TYPE: PRT
<213> ORGANISM: Sus scrofa

<400> SEQUENCE: 30

Arg Val Ala Pro Glu Glu His Pro Thr Leu
1               5                   10
```

BIOLOGICALLY ACTIVE PEPTIDE CONSISTING OF TYROSYL-SERYL-LEUCINE (YSL)

RELATED APPLICATIONS

This patent application is a divisional of U.S. patent application Ser. No. 10/237,405, filed Sep. 5, 2002 now U.S. Pat. No. 7,491,689, which is a continuation-in-part of U.S. patent application Ser. No. 10/178,684, filed Jun. 20, 2002 (abandoned), which is a continuation-in-part of U.S. patent application Ser. No. 09/904,492, filed Jul. 13, 2001 (abandoned). The disclosures of all of the above-referenced priority documents are incorporated by reference herein in their entireties.

The hard copy of the sequence listing submitted herewith and the corresponding computer readable form are both incorporated herein by reference in their entireties.

FIELD OF INVENTION

The present invention is related to the field of immunology. In particular, the present invention is directed to peptides and their pharmaceutical compositions which are capable of modulating immune responses.

BACKGROUND OF INVENTION

Spleen extracts from mammals have been used successfully for years as medical immune modulators. However, the molecular composition of such extracts is unknown and therefore the exact pharmacological actions of these extracts cannot be identified. The dosage response function also cannot be accurately titrated because of the intrinsic heterogeneous nature of these extracts. Because of such heterogeneity, active ingredients in spleen extracts cannot be singled out and their pharmacological actions cannot be fully utilized. And, no matter how careful the extraction process can be, there is always the possibility of transmission of diseases of animal origin to human if animal tissue is used as the raw material for extraction.

U.S. Pat. No. 3,992,364 to Kuhlmey describes a physiologically active polypeptide produced from an animal spleen extract. The exact sequence of the peptide was not disclosed and the preparation was described as being useful for decreasing cholesterol levels and increasing the 17 keto-steroid elimination of human patients.

SUMMARY OF INVENTION

It is an object of the present invention to identify biologically active polypeptides.

A study was conducted in which a number of peptides have been identified from a porcine spleen extract according to the method described in U.S. Pat. No. 3,992,364. The active fraction is also sold under the trade name "Polyerga". The peptides in the extract were separated by preparative HPLC followed by analysis using electrospray ionisation mass spectroscopy (ESMS) and matrix assisted laser desorption ionisation mass spectroscopy (MALDI-MS) at the W. M. Keck Foundation Biotechnology Resource Laboratory at Yale University. Once the identity of the peptides was found, they were individually synthesized by standard chemical methods. Using known animal and in vitro methods, the immunological function of these peptides was analyzed. The in vivo study of the effect of the peptides on immunity was performed using methods described in the following references. The peptides are given codes having the letters CMS followed by a number.

The peptide sequence and the corresponding ID numbers are shown in Table A. A total of 30 peptides have been identified as having in vivo biological activities. The effect of the peptides on kidney function, liver function, cancer and body weight was also analyzed.

TABLE A

| Sequence Listing ID No. | Peptide Name | Peptide Sequence |
|---|---|---|
| 1 | CMS001 | Pro Thr Thr Lys Thr Tyr Phe Pro His Phe |
| 2 | CMS002 | Val Val Tyr Pro Trp Thr Gln Arg Phe |
| 3 | CMS008 | Lys Ala Val Gly His Leu Asp Asp Leu Pro Gly Ala Leu |
| 4 | CMS010 | Val Ala Pro Glu Glu His Pro Thr Leu Leu Thr Glu Ala Pro Leu Asn Pro Lys |
| 5 | CMS012 | Leu Gly Met Glu Ala Cys Gly Ile His Glu Thr Thr Tyr |
| 6 | CMS013 | Leu Arg Val Ala Pro Glu Glu His Pro Val Leu |
| 7 | CMS014 | Ala Ala His His Pro Asp Asp Phe Asn Pro Ser Val |
| 8 | CMS015 | Pro Ser Ile Val Gly Arg Pro Arg His Gln Gly Val Met |
| 9 | CMS016 | Ile Gly Met Glu Ser Ala Gly Ile His Glu Thr Thr Tyr |
| 10 | CMS018 | Val Gly Met Gly Glu Lys Asp Ser Tyr |
| 11 | CMS019 | Val Gly Met Gly Gln Lys Asp Ser Tyr |
| 12 | CMS020 | Val Gly Met Gly Gln Lys Asp Ser Tyr Val |
| 13 | CMS021 | Met Ala Thr Ala Ala Ser Ser Ser Ser Leu |
| 14 | CMS022 | Tyr Ser Phe |
| 15 | CMS023 | Ala Ala Phe |
| 16 | CMS024 | Tyr Ser Leu |
| 17 | CMS026 | Thr Thr Tyr Asn Ser Ile Met |
| 18 | CMS027 | Phe Glu Glu Asn Met |
| 19 | CMS028 | Phe Glu Pro Ser Phe |
| 20 | CMS029 | Phe Asn Glu Glu |
| 21 | CMS030 | Phe Glu Glu Met |
| 22 | CMS032 | Phe Glu Glu Glu |
| 23 | CMS033 | Phe Glu Ser Phe |
| 24 | CMS034 | Pro Glu Asn Phe |
| 25 | CMS035 | Phe Val Asn Asp |

TABLE A-continued

| Sequence Listing ID No. | Peptide Name | Peptide Sequence |
|---|---|---|
| 26 | CMS036 | Phe Gln Pro Ser Phe |
| 27 | CMS003 | Phe Asn Phe Val Pro Pro |
| 28 | CMS007 | Ala Gly Asp Asp Ala Pro Arg Ala Val Phe |
| 29 | CMS009 | Leu Arg Val Ala Pro Glu Glu His Pro Thr Leu |
| 30 | CMS011 | Arg Val Ala Pro Glu Glu His Pro Thr Leu |

Accordingly, one aspect of the present invention relates to substantially pure peptides having sequences identified as sequence ID No.1 to sequence ID No.30. Thus the present invention also relates to a substantially pure peptide comprising an amino acid sequence selected from the group consisting of SEQ ID NOs. 1-30. It also relates to a substantially pure peptide consisting essentially of an amino acid sequence selected from the group consisting of SEQ ID NOs. 1-30. The invention also relates to a substantially pure peptide consisting of an amino acid sequence selected from the group consisting of SEQ ID NOs. 1-30. In a specific embodiment, the peptides can modulate, but not limited to modulating, one or more of the following: immune activity; hepatitis infection, including but not limited to hepatitis B infection; nephritis; the growth of a cancer, including but not limited to sarcoma, liver cancer, leukemia and melanoma; and body weight.

Another aspect of the present invention relates to substantially pure peptides that are functional derivatives of peptides having sequences identified as sequence ID No.1 to 30. Thus the present invention relates also to a substantially pure peptide comprising an amino acid sequence which is a functional derivative of a biologically active peptide, this biologically active peptide having an amino acid sequence selected from the group consisting of SEQ ID NOs. 1-30. It also relates to a substantially pure peptide consisting essentially of an amino acid sequence which is a functional derivative of a biologically active peptide, this biologically active peptide having an amino acid sequence selected from the group consisting of SEQ ID NOs. 1-30. The invention also relates to a substantially pure peptide consisting of an amino acid sequence which is a functional derivative of a biologically active peptide, this biologically active peptide having an amino acid sequence selected from the group consisting of SEQ ID NOs. 1-30. In a specific embodiment, the peptides that are functional derivatives can modulate, but not limited to modulating, one or more of the following: immune activity; hepatitis infection, including but not limited to hepatitis B infection; nephritis; the growth of a cancer, including but not limited to sarcoma, liver cancer, leukemia and melanoma; and body weight.

Another aspect of the present invention relates to nucleic acids that have sequences coding for the peptides identified above as sequence ID No.1 to 30. A further aspect of the present invention relates to expression vectors that contain the nucleic acid sequences of the peptides shown below as sequence ID No.1 to 30. Thus, this aspect of the present invention also relates to a genetic vector comprising a nucleotide sequence encoding a peptide comprising an amino acid sequence selected from the group comprising of SEQ ID NOs. 1-30. It also relates to a genetic vector comprising a nucleotide sequence encoding a peptide consisting essentially of an amino acid sequence selected from the group consisting of SEQ ID NOs. 1-30. The invention also relates to a genetic vector comprising a nucleotide sequence encoding a peptide comprising a functional derivative of a biologically active amino acid sequence selected from the group consisting of SEQ ID NOs. 1-30. It also relates to a genetic vector comprising a nucleotide sequence encoding a peptide consisting essentially of a functional amino acid sequence which is a functional derivative of a biologically active amino acid sequence selected from the group consisting of SEQ ID NOs. 1-30.

Yet another aspect of the present invention relates to hybrid peptides containing a leader peptide adjacent a peptide, the peptide comprising an amino acid sequence selected from the group consisting of SEQ ID NOs. 1-30. The present invention also relates to hybrid peptides containing a leader peptide adjacent a peptide, the peptide comprising a functional derivative of a biologically active peptide, this biologically active peptide having an amino acid sequence selected from the group consisting of SEQ ID NOs. 1-30.

The present invention also relates a genetic vector comprising a nucleotide sequence encoding a peptide comprising a leader amino acid sequence adjacent a peptide comprising a functional amino acid sequence which is a functional derivative of a biologically active amino acid sequence selected from the group consisting of SEQ ID NOs. 1-30. It also relates to a genetic vector comprising a nucleotide sequence encoding a peptide comprising a leader amino acid sequence adjacent a peptide consisting essentially of a functional amino acid sequence which is a functional derivative of a biologically active amino acid sequence selected from the group consisting of SEQ ID NOs. 1-30.

In a specific embodiment, the peptides produced in any of the above-described genetic vectors can modulate, but not limited to modulating, one or more of the following: immune activity; hepatitis infection, including but not limited to hepatitis B infection; nephritis; the growth of a cancer, including but not limited to sarcoma, liver cancer, leukemia and melanoma; and body weight.

Yet another aspect of the present invention relates to a micro-organism with a genome comprising a nucleotide sequence encoding a peptide comprising an amino acid sequence selected from the group consisting of SEQ ID NOs. 1-30. It also relates to a micro-organism with a genome comprising a nucleotide sequence encoding a peptide consisting essentially of an amino acid sequence selected from the group consisting of SEQ ID NOs. 1-30.

Yet another aspect of the present invention relates to a micro-organism with genetic material comprising a nucleotide sequence encoding a peptide, preferably an exogenous peptide comprising a functional amino acid sequence which is a functional derivative of a biologically active amino acid sequence selected from the group consisting of SEQ ID NOs. 1-30. It also relates to a micro-organism with a genetic composition comprising a nucleotide sequence encoding an exogenous peptide consisting essentially of a functional amino acid sequence which is a functional derivative of a biologically active amino acid sequence selected from the group consisting of SEQ ID NOs. 1-30. Exogenous peptide as used herein refers to a peptide having an amino acid sequence that is different from any other peptides normally expressed by the micro-organism in its natural, unmodified form.

Yet another aspect of the present invention relates to a micro-organism with a genetic composition comprising a nucleotide sequence encoding a peptide, preferably an exogenous hybrid peptide comprising a leader amino acid sequence adjacent a peptide, the peptide comprising an amino acid sequence selected from the group consisting of SEQ ID NOs. 1-30. It also relates to a micro-organism with a genome comprising a nucleotide sequence encoding a hybrid peptide comprising a leader amino acid sequence adjacent a peptide consisting essentially of an amino acid sequence selected from the group consisting of SEQ ID NOs. 1-30.

Yet another aspect of the present invention relates to a micro-organism with a genetic composition comprising a nucleotide sequence encoding an exogenous hybrid peptide comprising a leader amino acid sequence adjacent a peptide, the peptide comprising a functional amino acid sequence which is a functional derivative of a biologically active amino acid sequence selected from the group consisting of SEQ ID NOs. 1-30. It also relates to a micro-organism with a genetic composition comprising a nucleotide sequence encoding an exogenous hybrid peptide comprising a leader amino acid sequence adjacent a peptide consisting essentially of a functional amino acid sequence which is a functional derivative of a biologically active amino acid sequence selected from the group consisting of SEQ ID NOs. 1-30.

In a specific embodiment, the peptides produced in any of the above-described micro-organism can modulate, but not limited to modulating, one or more of the following: immune activity; hepatitis infection, including but not limited to hepatitis B infection; nephritis; the growth of a cancer, including but not limited to sarcoma, liver cancer, leukemia and melanoma; and body weight.

Yet another aspect of the present invention relates to a pharmaceutical composition comprising a substantially pure peptide comprising an amino acid sequence selected from the group consisting of SEQ ID NOs. 1-30. The invention also relates to pharmaceutical composition comprising a substantially pure peptide consisting essentially of an amino acid sequence selected from the group consisting of SEQ ID NOs. 1-30.

The present invention also relates to a pharmaceutical composition comprising a substantially pure peptide comprising a functional derivative of a biologically active peptide, this biologically active peptide having an amino acid sequence selected from the group consisting of SEQ ID NOs. 1-30. It also relates to a pharmaceutical composition comprising a substantially pure peptide consisting essentially of a functional derivative of a biologically active peptide, this biologically active peptide having an amino acid sequence selected from the group consisting of SEQ ID NOs. 1-30. It further relates to pharmaceutical composition comprising a substantially pure peptide consisting of functional derivative of a biologically active peptide, this biologically active peptide having an amino acid sequence selected from the group consisting of SEQ ID NOs. 1-30.

In a specific embodiment, the peptides present in any of the above-described pharmaceutical compositions can modulate, but not limited to modulating, one or more of the following: immune activity; hepatitis infection, including but not limited to hepatitis B infection; nephritis; the growth of a cancer, including but not limited to sarcoma, liver cancer, leukemia and melanoma; and body weight.

Yet a further aspect of the present invention relates to a method of making a pharmaceutical composition comprising providing a substantially pure peptide comprising an amino acid sequence selected from the group consisting of SEQ ID NOs. 1-30; and mixing said substantially pure peptide with a pharmaceutically acceptable carrier. It also relates to a method of making a pharmaceutical composition comprising providing a substantially pure peptide consisting essentially of an amino acid sequence selected from the group consisting of SEQ ID NOs. 1-30.

Another aspect of the present invention is a method of making a pharmaceutical composition comprising providing a substantially pure peptide comprising an amino acid sequence which is a functional derivative of a biologically active peptide, this biologically active peptide having an amino acid sequence selected from the group consisting of SEQ ID NOs. 1-30; and mixing said substantially pure peptide with a pharmaceutically acceptable carrier.

It further relates to a method of making a pharmaceutical composition comprising providing a substantially pure peptide consisting essentially of an amino acid sequence which is a functional derivative of a biologically active peptide, this biologically active peptide having an amino acid sequence selected from the group consisting of SEQ ID NOs. 1-30; and mixing the substantially pure peptide with a pharmaceutically acceptable carrier.

In connection with any of the above-described method, the peptide can modulate, but not limited to modulating, one or more of the following: immune activity; hepatitis infection, including but not limited to hepatitis B infection; nephritis; the growth of a cancer, including but not limited to sarcoma, liver cancer, leukemia and melanoma; and body weight.

Yet a further aspect of the present invention relates to a method of treatment of a human comprising administering a pharmaceutically effective dose of a substantially pure peptide comprising an amino acid sequence selected from the group consisting of SEQ ID NOs. 1-30 to a human. It also relates to a method of treatment of a human comprising administering a pharmaceutically effective dose of a substantially pure peptide comprising an amino acid sequence which is a functional derivative of a biologically active peptide, this biologically active peptide having an amino acid sequence selected from the group consisting of SEQ ID NOs. 1-30.

In a specific embodiment, the peptides used for the treatment of human described above may be used to modulate, but not limited to modulating, one or more of the following human conditions: immune activity; hepatitis infection, including but not limited to hepatitis B infection; nephritis; the growth of a cancer, including but not limited to sarcoma, liver cancer, leukemia and melanoma; and body weight.

In connection with any of the above-described nucleic acid sequences, the peptides and/or hybrid peptides expressed from these nucleic acid sequences can modulate, but not limited to modulating, the following: immune activity; hepatitis infection, including but not limited to hepatitis B infection; nephritis; the growth of a cancer, including but not limited to sarcoma, liver cancer, leukemia and melanoma; and body weight.

Another aspect of the present invention relates to the method of treating diseases comprising administering a pharmaceutically effective dose of a substantially pure peptide having sequence ID No.1 to sequence ID No.30. In a specific embodiment, the peptides so administered can modulate, but not limited to modulating, the following: immune activity; hepatitis infection, including but not limited to hepatitis B infection; nephritis; the growth of a cancer, including but not limited to sarcoma, liver cancer, leukemia and melanoma; and body weight.

As described above, another embodiment of the present invention is a peptide or polypeptide consisting essentially of a peptide of the present invention. As used herein, the terminology "consisting essentially of" refers to a peptide or polypeptide which includes the amino acid sequence of the peptides of the present invention along with additional amino acids at the carboxyl and/or amino terminal ends and which maintains the activity of the peptides of the present invention provided herein. Thus, as a non-limiting example, where the activity of the peptide of the present invention is to modulate immune activity, a peptide or polypeptide "consisting essentially of" the peptide of the present invention will possess the activity of modulating immune activity as provided herein with respect to that peptide and will not possess any characteristics which materially reduces the ability of the peptide or polypeptide to modulate immune activity or which constitutes a material change to the basic and novel characteristics of the peptide as a modulator of immune activity. Thus, in the foregoing example, a full length naturally occurring polypeptide which has a primary activity other than modulating immune activity and which contains the amino acid sequence of a peptide of the present invention somewhere therein would not constitute a peptide or polypeptide "consisting essentially of" a peptide of the present invention. Likewise, in the foregoing example, a genetically engineered peptide or polypeptide which has a primary activity other than modulating immune activity but includes the amino acid sequence of a peptide of the present invention somewhere therein would not constitute a peptide or polypeptide "consisting essentially of" a peptide of the present invention.

Besides the example of immune activity modulation used for illustration above, the foregoing definition also applies to all the peptides of the present invention with respect to the activities provided for such peptides. In particular, the foregoing definition applies to peptides of the invention having activities in modulating the extent of a viral infection, modulating the extent of a hepatitis infection, modulating the extent of nephritis, modulating the growth of a cancer, or modulating body weight as set forth in the detailed description below.

Those skilled in the art can readily determine whether a peptide or polypeptide consists essentially of a peptide of the present invention under the foregoing definitions by measuring the activity of the peptide or polypeptide using the assays for modulation of immune activity, modulating the extent of a viral infection, modulating the extent of a hepatitis infection, modulating the extent of nephritis, modulating the growth of a cancer, or modulating body weight which are provided herein with respect to a particular peptide of the present invention.

In the preferred embodiment, the terminology "consisting essentially of" may also refer to peptides or polypeptides which have less than 20 amino acid residues in addition to the peptide according to the present invention. In a more preferred embodiment, the same terminology refers to a peptides with less than 15 amino acid residues in addition to the peptide according to the instant invention. In an even more preferred embodiment, the same terminology refers to a peptides with less than 10 amino acid residues in addition to the peptide according to the instant invention. In another preferred embodiment, the same terminology refers to peptides or polypeptides with less than 6 amino acids in addition to one of the peptide of the present invention. In another preferred embodiment, the same terminology refers to peptides or polypeptides with less than 4 amino acids in addition to one of the peptide of the present invention. In the most preferred embodiment, the same terminology refers to peptides or polypeptides with less than 2 amino acids in addition to one of the peptide of the present invention.

DETAILED DESCRIPTION

The peptides can be readily synthesized by standard synthetic methods from L-amino acids, but may also be synthesized by genetic engineering methods using nucleic acids that have sequences encoding the individual peptides.

I. Biological Activity

In order to investigate the possible biological activity of peptides, the immunological effect of the peptides on animal model was examined, with procedures compliant to the "Principles of Pre-clinical Research of New Drugs" issued by Ministry of Health of People's Republic of China[1].

The T lymphocyte transformation test, NK cell cytotoxicity activity test, and the T lymphocyte IL-2 and IFN-γ secretion test were used to detect any possible effect of peptides on specific cellular immune function. The carbon particle clearance test was used to detect any possible effect of peptides on non-specific cellular immune function. The Sheep Red Blood Cell (SRBC) hemolysis test was used to detect any possible effect of peptides on humoral immune function. The immunity organ weight test was used to detect any possible effect of peptides at the organ level.

In this study, the saline group was used as negative control, while the IL-2 and IFN-γ groups were used as positive controls, since IL-2 and IFN-γ are well-studied immunostimulants[10]. Four arbitrary concentrations of sample peptides were used in this study, to cover a 1000 fold dosage range. Due to the intrinsic complexity of in vivo immunological response, and the lack of prior knowledge on the dosage versus response function, therefore any statistically significant difference over the negative control in any of the dosage groups has been scored as positive biological activity.

Results of this study were as follows:

1. Peptides CMS001, CMS002, CMS003, CMS007, CMS008, CMS009, CMS010, CMS011, CMS012, CMS015, CMS019, CMS021, CMS029, and CMS034 were found to be able to enhance T lymphocyte transformation, having statistically significant difference from the saline normal control group. Peptides CMS014 and CMS036 were also found to be able to inhibit T lymphocyte transformation, having statistically significant difference from the saline normal control group.
2. Peptides CMS001, CMS002, CMS003, CMS008, CMS009, CMS010, CMS011, CMS012, CMS013, CMS015, CMS016, CMS020, CMS021, CMS022, CMS023, CMS024, CMS026, CMS027, CMS028, CMS029, CMS030, CMS032, CMS033, CMS034, CMS035, and CMS036 were found to be able to increase the cytotoxic activity of NK cells, having statistically significant difference from the saline normal control group. Peptides CMS008 and CMS012, at suitable concentration, were also found to be able to decrease the cytotoxic activity of NK cells, having statistically significant difference from the saline normal control group.
3. Peptides CMS001, CMS003, CMS007, CMS009, CMS010, CMS011, CMS012, CMS015, CMS020, CMS022, and CMS034 were found to be able to enhance the secretion of interleukin-2 (IL-2) by T lymphocytes, having statistically significant difference from the saline normal control group.
4. Peptides CMS001, CMS003, CMS009, CMS010, CMS011, CMS012, CMS013, CMS016, CMS021, CMS022, and CMS028 were found to be able to enhance the secretion of IFN by T lymphocytes, having statistically significant difference form the saline normal control group.
5. Peptides CMS001, CMS002, CMS003, CMS007, CMS008, CMS009, CMS010, CMS011, CMS012, CMS013, CMS014, CMS015, CMS016, CMS018, CMS019, CMS020, CMS021, CMS022, CMS023, CMS024, CMS026, CMS027, CMS028, CMS029, CMS030, CMS032, CMS033, CMS034, CMS035, and CMS036 were found to be able to enhance the synthesis of anti-SRBC antibody upon the antigenic challenge, having statistically significant difference from the saline normal control group. Peptides CMS002, CMS003, CMS009, CMS010, CMS011, CMS013, CMS014, CMS015, CMS018, CMS019, CMS020, CMS026, CMS028, CMS029, CMS030, CMS034, and CMS036, at suitable concentration, were also found to be able to inhibit the synthesis of anti-SRBC antibody upon the antigenic challenge, having statistically significant difference from the saline normal control group.

6. Peptides CMS003, CMS008, CMS009, CMS010, CMS011, CMS013, CMS016, CMS018, CMS019, CMS020, CMS022, CMS024, CMS027, CMS030, CMS035, CMS036 were found to be able to enhance the phagocytotic activity of mononuclear phagocyte, having statistic significant difference from the saline normal control group.

7. Peptides CMS001, CMS002, CMS008, CMS010, CMS012, CMS013, CMS014, CMS015, CMS016, CMS018, CMS019, CMS020, CMS021, CMS022, CMS023, CMS024, CMS026, CMS027, CMS028, CMS029, CMS030, CMS032, CMS033, CMS034, CMS035, and CMS036 were found to be able to increase the weight of the thymus gland, having statistically significant difference from the saline normal control group.

8. Peptides CMS019, CMS020, and CMS030 were found to be able to increase the weight of the spleen, having statistically significant difference from the saline normal control group. Peptides CMS001, CMS003, CMS007, CMS008, CMS009, CMS010, CMS011, CMS013, CMS014, CMS015, CMS021, CMS023, CMS024, CMS027, CMS029, and CMS036, at suitable concentration, were also found to be able to decrease the weight of the spleen, having statistically significant difference from the saline normal control group.

The materials and methods used to analyze the effect of the peptides on mouse are described below.

Materials

1. Experimental Animal

BALB/c Mice, 18-22 g weight, 50% female and 50% male, provided by Experimental Animal Center, National Institute of Medical Science, PR China.

2. Administration recombinant mouse IFN-γ (rmIFN-γ) group: $3 \times 10^5$ IU/kg/day recombinant human IL (rhIL)-2 group: $3 \times 10^5$ IU/kg/day Saline group: 0.5 ml/each/day peptide dose I group: 500 μg/kg/day peptide dose II group: 50 μg/kg/day peptide dose III group: 5 μg/kg/day peptide dose IV group: 0.5 μg/kg/day The above substances were all dissolved in 0.5 ml saline and injected intraperitoneal (i.p.) for 15 continuous days, once per day.

3. Main Reagents

The peptides were custom manufactured by American Peptide Company, Inc., USA

Fetal bovine serum, and RPMI-1640 cell culture medium, Gibco, USA

MTT, and ConA, Sigma, USA rmIFN-γ, Beijing Biotech Inc., China rhIL-2, Shanghai Huaxin Biotech Inc., China Lymphocyte separation solution, Research Institute of Hematologic Disease, National Institute of Medical Science, PR China Vesicular Stomatitis Virus (VSV), IFN-γ and IL-2 standard sample, National Institute For The Control Of Pharmaceutical And Biological Products, PR China HT-2 cell and L929 cell, gift from Prof WF Chen of Beijing University Department of Immunology, PR China

I. METHOD

1. The Effect of Peptides on Cellular Immunity 1.1 Preparation of Spleen Cell Suspension[1,2]

The BALB/c mice were randomly divided into the peptide, IFN, IL-2, and saline groups. Ten mice per group. The day after the last test substance administration, the mice were sacrificed by cervical dislocation. The spleen was isolated aseptically and manually dispersed in cold D-Hank's solution using an injection needle. The dispersed cell suspension was further sieved through a 100 gauge 150 μm diameter stainless steel sieve. After centrifugation at 200 g for 10 minutes, the supernatant was discarded. The cell pellet was re-suspended in 10 volume of Tris-$NH_4Cl$ buffer and then kept standing still for 10 minutes at room temperature. The suspended cells were collected by centrifugation at 150 g for 10 minutes. The cells were washed 2-4 times with cold D-Hank's solution by re-suspending and collecting by centrifugation with condition as described above. The washed cells were then diluted to the desired cell densities by RPMI-1640 culture medium, containing 10% fetal bovine serum.

1.2 The Effect of Peptides on T Lymphocyte Transformation[1,2]

Spleen cells of density $1 \times 10^6$/ml were placed onto a 96 wells cell culture plate, 100 μl/well, three parallel wells each of the assay sample and control sample per mouse. To the assay wells, 100 μl/well ConA of 100 μg/ml in RPMI-1640 was added, and 100 μl/well plain RPMI-1640 was used for the controls. The cells were incubated for 66 hrs at 37° C., 5% $CO_2$. The cells were then pelleted by centrifugation at 150 g for 10 minutes. The supernatant was collected and stored at −20° C. for cytokines IL-2 and IFN determination.

50 μl/well MTT of 1 mg/ml in RPMI-1640 was added to the cell pellet and the cells re-suspended by shaking for 2 minutes. The incubation was continued for 4 hours. The supernatant was discarded after centrifugation at 150 g for 10 minutes. 120 μl 40 mM HCl-2-propanol was added to the cell pellet and shaken for 3 minutes. to obtain $OD_{570}$ nm of each well referenced at 630 nm. An ELISA reader was used Calculation:

Each mouse formed three assay wells and three control wells. The Stimulation Index (SI) of each mouse was obtained by first deriving the average OD of the three parallel wells, then dividing the value of the assay wells by the control wells.

1.3 The effect of peptides on NK cell activity[3,4]

Mice spleen cells were prepared to $4 \times 10^6$/ml as described in section 1.1 above. Target cells YAC-1 were brought to log phase and adjusted to $1 \times 10^5$/ml. Using a 96 wells cell culture plate, 100 μl mouse spleen cells and 100 μl culture medium were added to the control well containing only the spleen cells; 100 μl target cells and 100 μl culture medium were added to the control well containing only target cells; 100 μl mouse spleen cells and 100 μl target cells were added to the NK activity assay well. Three parallel sets of the above were prepared per mouse.

Samples were centrifuged at 150 g for 10 minutes to collect the cells. The supernatant was discarded and 50 μl/well MTT of 1 mg/ml was added. The reaction mixture was then shaken for 2 minutes, and incubated at 37° C., 5% $CO_2$ for 4 hours. The supernatant was discarded after centrifugation at 150 g for 10 minutes. 120 μl 40 mM HCl-2-propanol was added and shaken for 3 minutes. An ELISA reader was used to obtain $OD_{570nm}$ of each well referenced at 630 nm.

Calculation:

Each mouse has 9 wells: three spleen cells only control, three target cells only control, and three assay wells with both spleen and target cells. The NK cell activity index of each mouse was obtained by first deriving the average OD of the three parallel wells of each combination, then applying this average OD to the following formula:

NK cell activity index=[1−(average OD of spleen and target cell well−average OD of spleen cell only well)÷(average OD of target cell only well)]× 100%

1.4 The Effect of Peptides on the Activity T Lymphocyte in Secreting IL-2[5]

HT-2 cells at log phase were collected by centrifugation at 150 g for 10 minutes, and washed three times with cold Hank's solution by re-suspension and centrifugation. The collected HT-2 cells were re-suspended in RPMI-1640 and incubated at 37° C., 5% $CO_2$ for 30 minutes. The cells were further washed twice with RPMI-1640 by re-suspension and centrifugation, and re-suspended to final concentration of $2×10^5$/ml with RPMI-1640.

The supernatant obtained in section 1.2 were diluted to the following percentage with RPMI-1640: 100%, 50%, 25%, 12.5%, 6.25%, and 3.125%.

rIL-2 was diluted to the following concentration with RPMI-1640: 500 IU/ml, 250 IU/ml, 125 IU/ml, 62.5 IU/ml, 31.25 IU/ml, and 15.5 IU/ml.

A 96 well cell culture plate was set up with three parallel wells per combination:

Negative control: 100 μl RPMI-1640+100 μl HT-2 cell suspension rIL-2 standard: 100 μl rIL-2 solution+100 μl HT-2 cell suspension Assay well: 100 μl diluted supernatant+100 μl HT-2 cell suspension The plate was incubated at 37° C., 5% $CO_2$ for 68 hours, then centrifuged at 150 g for 15 minutes and the supernatant removed. 100 μl 0.5 mg/ml MTT in RPMI-1640 without phenolsulfonphthalein was added into each well. After shaking for 3-4 minutes to re-suspend the cells, continue to incubate for another 4 hours. Samples were then centrifuged at 150 g for 15 minutes and the supernatant was removed. To each well, 120 μl 40 mM HCl-2-propanol was added, mixed for 3-4 minutes and OD analyzed at 570 nm, referenced at 630 nm with an ELISA plate reader.

Calculation:

The average OD of the three parallel wells of each dilution was taken and plotted against concentration on a semi-log paper, concentration on the X-axis. The concentration at 50% OD saturation was obtained for both the testing supernatant and rIL-2.

Sample IL-2 activity=(sample dilution at 50% maximum action÷rIL-2 standard dilution at 50% maximum action)×activity of rIL-2 standard at 50% maximum action (IU/ml)

1.5 The Effect of Peptides on the Activity of T Lymphocyte in Secreting Interferon (IFN)[6]

The supernatant from the section 1.2 was diluted with RPMI-1640 culture medium to the following percentages: 100%, 50%, 25%, 12.5%, 6.25%, and 3.125%.

The recombinant interferon (rIFN) standard was diluted with RPMI-1640 to the following concentrations: 500 IU/ml, 250 IU/ml, 125 IU/ml, 62.5 IU/ml, 31.25 IU/ml, and 15.5 IU/ml.

Target cells L929 at log phase were adjusted to $2×10^5$/ml with RPMI-1640, with treatment same as the HT-2 cell described in section 1.4. Stock VSV was also adjusted to 100 $TCID_{50}$ with RPMI-1640.

The following on a 96 well culture plate was set up, three parallel wells per combination:

Negative control well: 150 μl RPMI-1640+100 μl L929

Positive control well: 100 μl RPMI-1640+100 μl L929+50 μl VSV rIFN activity well: 100 μl rIFN standard+100 μl L929+50 μl VSV assay well: 100 μl diluted supernatant+100 μl L929+50 μl VSV Samples were incubated at 37° C., 5% $CO_2$ for 24 hours. The positive control wells were observed periodically under inverted microscope to confirm cell lysis, then collected, washed, and OD of all wells was read same as described in section 1.4.

Calculation:

Concentrations at 50% maximum action were obtained same way as section 1.4. Calculate IFN activity of sample as following:

Sample IFN activity=(sample dilution at 50% maximum action÷rIFN standard dilution at 50% maximum action)×standard rIFN activity at that 50% maximum action (IU/ml)

2. The Effect of Peptides on Antibody Formation[7]

Sheep red blood cells (SRBC) were prepared by collecting blood from cervical vein and put into a sterile flask with glass beads. The flask was shaken for 3 minutes and the blood then mixed with Alsever solution (glucose 2.05g, NaCl 0.4 g, Sodium Citrate 0.8 g, adjust to 100 ml with distilled water) and stored at 4° C. Immediately before use, samples were centrifuged at 130 g, 5 minutes to collect the SRBC. The cells were washed two times by re-suspension and centrifugation in normal saline. Then the cell pellet was collected by centrifugation at 180 g for 10 minutes and re-suspended in saline to make the final working SRBC suspension, 2% (v/v).

Complement was prepared by adding 10 volumes of fresh Cavy serum into one volume centrifuge packed SRBC, and then gently shaking for 30 minutes at 4° C. The SRBC was removed by centrifugation at 200 g for 10 minutes. 10 volumes of normal saline were added to obtain the working complement solution.

The BALB/c mice were randomly divided into the peptide group, IFN group, IL-2 group, and saline group, 10 mice per group. The test substances were administered as described in section 1.1, plus intraperitoneal injection 0.2 ml SRBC per mouse on day 12. On the day after the last test substance administration (day 16), blood was collected from the eye canthus and left at room temperature for one hour for serum exudation. After centrifugation at 200 g for 10 minutes, the serum was diluted by 500 times with normal saline.

To 1 ml diluted mouse serum of each mouse, 0.5 ml SRBC suspension was added. Ice cold. Then 1 ml working complement solution was added and incubated at 37° C. water bath for 10 minutes. Reactions were terminated by ice cold. Samples were then centrifuged at 200 g for 10 minutes to obtain the supernatant.

To 1 ml of this supernatant, 3 ml Drabkin solution was added and left at room temperature for 10 minutes. $OD_{540nm}$ was obtained.

Calculation:

Reference $OD_{540nm}$ was obtained by mixing 0.25 ml SRBC suspension with Drabkin solution to 4 ml and placed at room temperature for 10 minutes before $OD_{540nm}$ was taken.

Sample serum index=($OD_{540nm}$ of test sample÷reference $OD_{540nm}$)×500

3. The Effect of Peptides on the Phagocytosis Function of Mononuclear Phagocyte and the Weight of Immune Organ[8,9].

On the next day after the last test substance administration (day 16), the mice were injected with 0.1 ml/kg body weight India ink (5 times dilution with normal saline) from the tail vein.

One minute and five minutes after Indian ink injection, 20 μl blood was obtained from the eye canthus with a heparinized tubing. The blood was mixed with 2 ml 0.1% w/v $Na_2CO_3$ and then $OD_{680nm}$ obtained. The outline clear index K was calculated by the following formula:

$K=(\lg A_1 - \lg A_2) \div (t2-t1)$

Key:
A1: OD680 nm at first minute
A2: OD680 nm at fifth minute
t2: 5 minutes
t2: 1 minute One day after the last test substance administration (day 16), the liver, spleen, and thymus gland were separated and blotted dry with filter paper and weighed. The phagocytosis index α was calculated as below:

$\alpha = (\sqrt[3]{K})(W \div W_{LS})$ key:
W: body weight
$W_{LS}$: weight of liver plus spleen
Thymus gland index (%)=(thymus weight/body weight)×100%
Spleen index (%)=(spleen weight/body weight)×100%

Results

Due to the large quantity of raw data involved, only the compiled end result are presented. The groups without statistically significant difference from the saline negative control are also omitted.

1. The Effect of Peptides on T Lymphocyte Transformation

At 500 μg/kg/day, CMS002, CMS007, CMS008, CMS009, CMS010, CMS012, CMS015, CMS019, CMS021, and CMS029 were found to be able to enhance T lymphocyte transformation, having statistically significant difference from the saline group (P<0.05). Among these peptides, CMS010 and CMS015 were found to have statistically significant difference from the IFN-γ group and IL-2 group (P<0.05) as shown in Table 1 below.

TABLE 1

| Group | N | X ± SD (stimulation index) |
|---|---|---|
| CMS002 | 8 | 1.8 ± 0.3* |
| CMS007 | 9 | 1.6 ± 0.1* |
| CMS008 | 9 | 1.7 ± 0.1* |
| CMS009 | 10 | 1.7 ± 0.2* |

TABLE 1-continued

| Group | N | X ± SD (stimulation index) |
|---|---|---|
| CMS010 | 9 | 2.0 ± 0.3*@^ |
| CMS012 | 9 | 1.6 ± 0.2* |
| CMS015 | 9 | 1.9 ± 0.3*@^ |
| CMS019 | 9 | 1.8 ± 0.3* |
| CMS021 | 10 | 1.6 ± 0.1* |
| CMS029 | 9 | 1.7 ± 0.3* |
| IFN-γ | 10 | 1.6 ± 0.2* |
| IL-2 | 10 | 1.7 ± 0.2* |
| Saline | 10 | 1.3 ± 0.1 |

*comparing to saline group P < 0.05
@comparing to IFN-γ group P < 0.05
^comparing to IL-2 group P < 0.05

At 50 μg/kg/day, CMS001, CMS002 and CMS003 were found to be able to stimulate T lymphocyte transformation, having statistically significant difference from saline group, IFN-γ group, and IL-2 group (P<0.05). CMS014 and CMS036 were found to be able to inhibit T lymphocyte transformation, having statistical significant difference from saline group (P<0.05). Data detailed in Table 2 below.

TABLE 2

| Group | N | X ± SD (stimulation index) |
|---|---|---|
| CMS001 | 10 | 2.2 ± 0.5*@^ |
| CMS002 | 10 | 2.6 ± 0.3*@^ |
| CMS003 | 8 | 2.2 ± 0.5*@^ |
| CMS014 | 9 | 1.0 ± 0.1* |
| CMS036 | 9 | 1.0 ± 0.1* |
| IFN-γ | 9 | 1.7 ± 0.2* |
| IL-2 | 10 | 1.8 ± 0.2* |
| Saline | 10 | 1.3 ± 0.1 |

*comparing to saline group P < 0.05
@comparing to IFN-γ group P < 0.05
^comparing to IL-2 group P < 0.05

At 5 μg/kg/day, CMS001, CMS003, CMS007, and CMS034 were found to be able to stimulate T lymphocyte transformation, having statistically significant difference from the saline group (P<0.05) as shown in Table 3.

TABLE 3

| Group | N | X ± SD (stimulation index) |
|---|---|---|
| CMS001 | 10 | 1.7 ± 0.2* |
| CMS003 | 10 | 1.6 ± 0.2* |
| CMS007 | 8 | 1.7 ± 0.1* |
| CMS034 | 9 | 1.5 ± 0.2* |
| IFN-γ | 10 | 1.6 ± 0.2* |
| IL-2 | 9 | 1.6 ± 0.1* |
| Saline | 10 | 1.3 ± 0.1 |

*comparing to saline group P < 0.05

At 0.5 μg/kg/day, CMS008, CMS010, and CMS011 were found to be able to stimulate T lymphocyte transformation, having statistically significant difference from the saline group (P<0.05) as shown in Table 4.

TABLE 4

| Group | N | X ± SD (stimulation index) |
|---|---|---|
| CMS008 | 10 | 1.7 ± 0.3* |
| CMS010 | 9 | 1.7 ± 0.3* |
| CMS011 | 10 | 1.6 ± 0.4* |
| IFN-γ | 10 | 1.6 ± 0.2* |

TABLE 4-continued

| Group | N | X ± SD (stimulation index) |
|---|---|---|
| IL-2 | 10 | 1.6 ± 0.1* |
| Saline | 10 | 1.3 ± 0.1 |

*comparing to saline group P < 0.05

2. The Effect of Peptide on NK Cell Cytotoxic Activity

At 500 μg/kg/day, CMS010, CMS013, CMS016, CMS023, CMS024, CMS026, CMS027, CMS028, CMS029, CMS030, CMS032, CMS033, CMS034, CMS035, and CMS036 were found to be able to increase NK cell cytotoxic activity, with statistically significant difference from the saline group (P<0.05). Among these peptides, CMS010, CMS016, and CMS030 were found to have statistically significant difference from the IFN-γ group and IL-2 group (P<0.05) as shown in Table 5.

TABLE 5

| Group | N | X ± SD (%) |
|---|---|---|
| CMS010 | 9 | 91 ± 4*@^ |
| CMS013 | 8 | 84 ± 9* |
| CMS016 | 9 | 91 ± 7*@^ |
| CMS023 | 10 | 79 ± 12* |
| CMS024 | 10 | 89 ± 8* |
| CMS026 | 10 | 89 ± 7* |
| CMS027 | 10 | 88 ± 8* |
| CMS028 | 10 | 90 ± 5* |
| CMS029 | 10 | 87 ± 4* |
| CMS030 | 10 | 91 ± 5*@^ |
| CMS032 | 10 | 87 ± 5* |
| CMS033 | 9 | 89 ± 8* |
| CMS034 | 11 | 85 ± 9* |
| CMS035 | 8 | 90 ± 10* |
| CMS036 | 10 | 88 ± 7* |
| IFN-γ | 10 | 77 ± 8* |
| IL-2 | 10 | 77 ± 8* |
| Saline | 8 | 63 ± 9 |

*comparing to saline group P < 0.05
@comparing to IFN-γ group P < 0.05
^comparing to IL-2 group P < 0.05

At 50 μg/kg/day, CMS001, CMS003, CMS015, CMS021, CMS026, and CMS035 were found to be able to increase NK cell cytotoxic activity, having statistically significant difference from the saline group (P<0.05). Among these peptides, CMS021 was found to have statistically significant difference from the IFN-γ group and IL-2 group (P<0.05). CMS012 was found to be able to inhibit NK cell cytotoxic activity, having statistically significant difference from the saline group (P<0.05). Data detailed in Table 6 below.

TABLE 6

| Group | N | X ± SD (%) |
|---|---|---|
| CMS001 | 10 | 85 ± 10* |
| CMS003 | 10 | 85 ± 6* |
| CMS012 | 9 | 40 ± 9* |
| CMS015 | 8 | 78 ± 8* |
| CMS021 | 8 | 88 ± 12*@^ |
| CMS026 | 10 | 76 ± 9* |
| CMS035 | 10 | 72 ± 9* |
| IFN-γ | 10 | 73 ± 10* |
| IL-2 | 10 | 74 ± 8* |
| Saline | 10 | 56 ± 8 |

*comparing to saline group P < 0.05
@comparing to IFN-γ group P < 0.05
^comparing to IL-2 group P < 0.05

At 5 μg/kg/day, CMS008, CMS009, CMS010, CMS011, CMS012, CMS020, CMS024, CMS034, and CMS036 were found to be able to increase NK cell cytotoxic activity, having statistically significant difference from the saline group (P<0.05). Among these peptides, CMS008 and CMS009 were found to have statistically significant difference from the IFN-γ group and IL-2 group (P<0.05) as shown in Table 7.

TABLE 7

| Group | N | X ± SD (%) |
|---|---|---|
| CMS008 | 10 | 92 ± 4*@^ |
| CMS009 | 8 | 92 ± 6*@^ |
| CMS010 | 10 | 82 ± 9* |
| CMS011 | 10 | 76 ± 10* |
| CMS012 | 10 | 85 ± 7* |
| CMS020 | 9 | 91 ± 6* |
| CMS024 | 9 | 78 ± 3* |
| CMS034 | 8 | 90 ± 5* |
| CMS036 | 10 | 75 ± 9* |
| IFN-γ | 10 | 80 ± 8* |
| IL-2 | 10 | 80 ± 8* |
| Saline | 10 | 60 ± 9 |

*comparing to saline group P < 0.05
@comparing to IFN-γ group P < 0.05
^comparing to IL-2 group P < 0.05

At 0.5 μg/kg/day, CMS002, CMS011, CMS012, CMS022, CMS028, and CMS035 were found to be able to increase NK cell cytotoxic activity, having statistically significant difference from the saline group (P<0.05). CMS008 was found to be able to inhibit NK cell cytotoxic activity, having statistical significant difference from the saline group (P<0.05). Data detailed in Table 8 below.

TABLE 8

| Group | N | X ± SD (%) |
|---|---|---|
| CMS002 | 8 | 76 ± 9* |
| CMS008 | 10 | 46 ± 12* |
| CMS011 | 9 | 79 ± 3* |
| CMS012 | 9 | 77 ± 6* |
| CMS022 | 10 | 73 ± 11* |
| CMS028 | 8 | 79 ± 3* |
| CMS035 | 10 | 76 ± 10* |
| IFN-γ | 10 | 72 ± 9* |
| IL-2 | 10 | 74 ± 10* |
| Saline | 11 | 58 ± 7 |

*comparing to saline group P < 0.05

3. The Effect of Peptides on the Activity of T Lymphocyte in Secreting IL-2

At 500 μg/kg/day, CMS007, CMS009, CMS010, and CMS015 were found to be able to promote IL-2 secretion from T lymphocyte, having statistically significant difference from the saline group (P<0.05). Among these peptides, CMS007 and CMS015 were found to have statistically significantly difference from the IL-2 group (P<0.05). And, CMS009 and CMS010 were also found to have statistically significant difference from both the IFN-γ group and IL-2 group (P<0.05) as shown in Table 9.

TABLE 9

| Group | N | X ± SD (IU) |
|---|---|---|
| CMS007 | 9 | 86 ± 15*^ |
| CMS009 | 10 | 114 ± 13*@^ |
| CMS010 | 9 | 125 ± 17*@^ |
| CMS015 | 9 | 85 ± 17*^ |

TABLE 9-continued

| Group | N | X ± SD (IU) |
|---|---|---|
| IFN-γ | 10 | 100 ± 18* |
| IL-2 | 10 | 70 ± 13* |
| Saline | 10 | 39 ± 10 |

*comparing to saline group P < 0.05
@comparing to IFN-γ group P < 0.05
^comparing to IL-2 group P < 0.05

At 50 μg/kg/day, CMS001 and CMS003 were found to be able to promote activity of T lymphocyte in secreting IL-2, having statistically significant difference from the saline group (P<0.05). Among these peptides, CMS003 was found to have statistically significant difference from the IL-2 group (P<0.05) as shown in Table 10.

TABLE 10

| Group | N | X ± SD (IU) |
|---|---|---|
| CMS001 | 10 | 60 ± 10* |
| CMS003 | 8 | 86 ± 9*^ |
| IFN-γ | 9 | 99 ± 16* |
| IL-2 | 10 | 72 ± 12* |
| Saline | 10 | 39 ± 10 |

*comparing to saline group P < 0.05
^comparing to IL-2 group P < 0.05

At 5 μg/kg/day, CMS007, CMS012, and CMS020 were found to be able to promote T lymphocyte in secreting IL-2, having statistically significant difference from the saline group (P<0.05) as shown in Table 11.

TABLE 11

| Group | N | X ± SD (IU) |
|---|---|---|
| CMS007 | 8 | 64 ± 12* |
| CMS012 | 9 | 65 ± 16* |
| CMS020 | 8 | 63 ± 11* |
| IFN-γ | 10 | 96 ± 14* |
| IL-2 | 10 | 77 ± 13* |
| Saline | 10 | 37 ± 9 |

*comparing to saline group P < 0.05

At 0.5 μg/kg/day, CMS010, CMS011, CMS012, CMS022, and CMS034 were found to be able to promote T lymphocyte in secreting IL-2, having statistically significant difference from the saline group (P<0.05). Among these peptides, CMS034 was found to have statistically significantly difference from the IL-2 group (P<0.05). And, CMS011 and CMS022 were also found to have statistically significant difference from both the IFN-γ group and IL-2 group (P<0.05) as shown in Table 12.

TABLE 12

| Group | N | X ± SD (IU) |
|---|---|---|
| CMS010 | 9 | 66 ± 11* |
| CMS011 | 10 | 101 ± 19*@^ |
| CMS012 | 8 | 59 ± 13* |
| CMS022 | 9 | 109 ± 14*@^ |
| CMS034 | 10 | 85 ± 10*^ |
| IFN-γ | 10 | 87 ± 15* |
| IL-2 | 10 | 73 ± 13* |
| Saline | 10 | 38 ± 13 |

*comparing to saline group P < 0.05
@comparing to IFN-γ group P < 0.05
^comparing to IL-2 group P < 0.05

4. The Effect of Peptides on the Activity of T Lymphocyte in Secreting IFN

At 500 μg/kg/day, CMS010, CMS013, and CMS016 were found to be able to promote T lymphocyte in secreting interferon (IFN), having statistically significant difference from the saline group, IFN-γ group, and IL-2 group (P<0.05) as shown in Table 13.

TABLE 13

| Group | N | X ± SD (IU) |
|---|---|---|
| CMS010 | 9 | 167 ± 13*@^ |
| CMS013 | 9 | 154 ± 15*@^ |
| CMS016 | 6 | 162 ± 19*@^ |
| IFN-γ | 10 | 139 ± 16* |
| IL-2 | 10 | 120 ± 13* |
| Saline | 10 | 65 ± 11 |

*comparing to saline group P < 0.05
@comparing to IFN-γ group P < 0.05
^comparing to IL-2 group P < 0.05

At 50 μg/kg/day, CMS001, CMS003, and CMS021 were found to be able to promote T lymphocyte in secreting IFN having statistically significant difference from the saline group (P<0.05). Among these peptides, CMS021 was found to have statistically significant difference from the IFN-γ group and IL-2 group (P<0.05) as shown in Table 14.

TABLE 14

| Group | N | X ± SD (IU) |
|---|---|---|
| CMS001 | 10 | 110 ± 15* |
| CMS003 | 8 | 106 ± 16* |
| CMS021 | 8 | 143 ± 17*@^ |
| IFN-γ | 9 | 125 ± 18* |
| IL-2 | 10 | 113 ± 17* |
| Saline | 10 | 61 ± 11 |

*comparing to saline group P < 0.05
@comparing to IFN-γ group P < 0.05
^comparing to IL-2 group P < 0.05

At 5 μg/kg/day, CMS009 and CMS012 were found to be able to promote T lymphocyte in secreting IFN having statistically significant difference from the saline group (P<0.05). Among these peptides, CMS009 was found to have statistically significant difference from the IL-2 group (P<0.05) as shown in Table 15.

TABLE 15

| Group | N | X ± SD (IU) |
|---|---|---|
| CMS009 | 10 | 121 ± 15*^ |
| CMS012 | 9 | 86 ± 9* |
| IL-2 | 9 | 105 ± 14* |
| Saline | 10 | 66 ± 10 |

*comparing to saline group P < 0.05
^comparing to IL-2 group P < 0.05

At 0.5 μg/kg/day, CMS010, CMS011, CMS022, and CMS028 were found to be able to promote T lymphocyte in secreting IFN, having statistically significant difference from the saline group (P<0.05). Among these peptides, CMS010 and CMS022 were found to have statistically significant difference from the IFN-γ group and IL-2 group (P<0.05) as shown in Table 16.

TABLE 16

| Group | N | X ± SD (IU) |
|---|---|---|
| CMS010 | 9 | 142 ± 18*@^ |
| CMS011 | 10 | 89 ± 18* |
| CMS022 | 9 | 145 ± 13*@^ |
| CMS028 | 10 | 96 ± 13* |
| IFN-γ | 10 | 124 ± 16* |
| IL-2 | 10 | 107 ± 13* |
| Saline | 10 | 64 ± 13 |

*comparing to saline group P < 0.05
@comparing to IFN-γ group P < 0.05
^comparing to IL-2 group P < 0.05

5. The Effect of Peptides on Antibody Formation

At 500 μg/kg/day, CMS002, CMS003, CMS007, CMS008, CMS009, CMS010, CMS011, CMS012, CMS013, CMS014, CMS015, CMS016, CMS018, CMS019, CMS020, CMS022, CMS023, CMS024, CMS029, CMS033, and CMS035 were found to be able to promote anti-SRBC antibody formation, having statistically significant difference from the saline group (P<0.05). Among these peptides, CMS002, CMS003, CMS007, CMS008, CMS013, CMS019, CMS024, and CMS035 were found to have statistically significant difference from the IFN-γ group (P<0.05). And, CMS009, CMS010, CMS011, CMS012, CMS014, CMS015, CMS016, CMS020, CMS023, CMS029, and CMS033 were also found to have statistically significant difference from both the IFN-γ group and IL-2 group (P<0.05) as shown in Table 17.

TABLE 17

| Group | N | X ± SD (Unit) |
|---|---|---|
| CMS002 | 10 | 87 ± 18*@ |
| CMS003 | 10 | 96 ± 18*@ |
| CMS007 | 10 | 69 ± 17*@ |
| CMS008 | 10 | 82 ± 15*@ |
| CMS009 | 10 | 113 ± 22*@^ |
| CMS010 | 10 | 112 ± 30*@^ |
| CMS011 | 8 | 188 ± 16*@^ |
| CMS012 | 8 | 141 ± 21*@^ |
| CMS013 | 10 | 80 ± 16*@ |
| CMS014 | 10 | 130 ± 24*@^ |
| CMS015 | 10 | 136 ± 22*@^ |
| CMS016 | 8 | 143 ± 38*@^ |
| CMS018 | 10 | 66 ± 16* |
| CMS019 | 10 | 91 ± 26*@ |
| CMS020 | 6 | 155 ± 35*@^ |
| CMS022 | 8 | 68 ± 31* |
| CMS023 | 9 | 110 ± 45*@^ |
| CMS024 | 8 | 75 ± 29*@ |
| CMS029 | 8 | 115 ± 22*@^ |
| CMS033 | 10 | 143 ± 27*@^ |
| CMS035 | 10 | 88 ± 16*@ |
| IFN-γ | 9 | 37 ± 10 |
| IL-2 | 10 | 71 ± 11* |
| Saline | 10 | 32 ± 7 |

*comparing to saline group P < 0.05
@comparing to IFN-γ group P < 0.05
^comparing to IL-2 group P < 0.05

At 50 μg/kg/day, CMS003, CMS011, CMS012, CMS013, CMS015, CMS021, CMS022, CMS023, CMS026, CMS027, CMS029, CMS030, CMS032, CMS033, CMS034, CMS035, and CMS036 were found to be able to promote anti-SRBC antibody formation, having statistically significant difference from the saline group (P<0.05). Among these peptides, CMS011, CMS013, and CMS015 were found to have statistically significant difference from the IFN-γ group (P<0.05). And, CMS021, CMS022, CMS023, CMS026, CMS027, CMS029, CMS030, CMS032, CMS033, CMS034, CMS035, and CMS036 were also found to have statistically significant difference from both the IFN-γ group and IL-2 group (P<0.05). CMS009 was found to be able to inhibit anti-SRBC antibody formation, having statistical significant difference from the saline group (P<0.05). Data detailed in Table 18 below.

TABLE 18

| Group | N | X ± SD (Unit) |
|---|---|---|
| CMS003 | 10 | 52 ± 11* |
| CMS009 | 8 | 13 ± 5* |
| CMS011 | 9 | 67 ± 9*@ |
| CMS012 | 8 | 50 ± 14* |
| CMS013 | 8 | 70 ± 9*@ |
| CMS015 | 10 | 54 ± 9*@ |
| CMS021 | 9 | 94 ± 20*@^ |
| CMS022 | 9 | 110 ± 16*@^ |
| CMS023 | 8 | 84 ± 11*@^ |
| CMS026 | 9 | 98 ± 9*@^ |
| CMS027 | 9 | 93 ± 11*@^ |
| CMS029 | 10 | 143 ± 13*@^ |
| CMS030 | 10 | 141 ± 33*@^ |
| CMS032 | 9 | 131 ± 24*@^ |
| CMS033 | 8 | 112 ± 15*@^ |
| CMS034 | 10 | 136 ± 11*@^ |
| CMS035 | 8 | 97 ± 10*@^ |
| CMS036 | 10 | 118 ± 11*@^ |
| IFN-γ | 9 | 37 ± 10 |
| IL-2 | 10 | 71 ± 11* |
| Saline | 10 | 32 ± 7 |

*comparing to saline group P < 0.05
@comparing to IFN-γ group P < 0.05
^comparing to IL-2 group P < 0.05

At 5 μg/kg/day, CMS001, CMS003, CMS007, CMS008, CMS009, CMS011, CMS012, CMS013, CMS015, CMS016, CMS019, CMS020, CMS021, CMS023, CMS024, CMS026, CMS027, CMS028, CMS029, CMS030, CMS032, CMS033, CMS034, CMS035, and CMS036 were found to be able to promote anti-SRBC antibody formation, having statistically significant difference from the saline group (P<0.05). Among these peptides, CMS003, CMS008, CMS009, CMS012, CMS013, CMS015, CMS016, CMS020, and CMS021 were found to have statistically significant difference from the IFN-γ group (P<0.05). And, CMS001, CMS007, CMS011, CMS019, CMS023, CMS024, CMS026, CMS027, CMS028, CMS029, CMS030, CMS032, CMS033, CMS034, CMS035, and CMS036 were also found to have statistically significant difference from both the IFN-γ group and IL-2 group (P<0.05) as shown in Table 19.

TABLE 19

| Group | N | X ± SD(Unit) |
|---|---|---|
| CMS001 | 9 | 110 ± 24*@ |
| CMS003 | 9 | 91 ± 24*@ |
| CMS007 | 9 | 122 ± 12*@^ |
| CMS008 | 9 | 97 ± 26*@ |
| CMS009 | 8 | 79 ± 18*@ |
| CMS011 | 10 | 115 ± 27*@^ |
| CMS012 | 10 | 81 ± 22*@ |
| CMS013 | 10 | 93 ± 28*@ |
| CMS015 | 8 | 94 ± 37*@ |
| CMS016 | 9 | 93 ± 32*@ |
| CMS019 | 10 | 118 ± 20*@^ |
| CMS020 | 10 | 89 ± 24*@ |
| CMS021 | 9 | 82 ± 30*@ |
| CMS023 | 10 | 166 ± 27*@^ |
| CMS024 | 7 | 171 ± 39*@^ |
| CMS026 | 9 | 191 ± 17*@^ |
| CMS027 | 9 | 117 ± 45*@^ |

TABLE 19-continued

| Group | N | X ± SD(Unit) |
|---|---|---|
| CMS028 | 10 | 121 ± 48*@^ |
| CMS029 | 9 | 147 ± 23*@^ |
| CMS030 | 9 | 158 ± 37*@^ |
| CMS032 | 9 | 157 ± 37*@^ |
| CMS033 | 7 | 128 ± 39*@^ |
| CMS034 | 8 | 172 ± 37*@^ |
| CMS035 | 9 | 176 ± 39*@^ |
| CMS036 | 8 | 179 ± 34*@^ |
| IFN-γ | 9 | 37 ± 10 |
| IL-2 | 10 | 71 ± 11* |
| Saline | 10 | 32 ± 7 |

*comparing to saline group P < 0.05
@comparing to IFN-γ group P < 0.05
^comparing to IL-2 group P < 0.05

At 0.5 μg/kg/day, CMS021, CMS023, CMS024, CMS027, and CMS033 were found to be able to promote anti-SRBC antibody formation, having statistically significant difference from the saline group (P<0.05). Among these peptides, CMS021 and CMS033 were found to have statistically significant difference from the IFN-γ group (P<0.05). And, CMS023, CMS024, and CMS027 were also found to have statistically significant difference from both the IFN-γ group and IL-2 group (P<0.05). Also, CMS002, CMS003, CMS009, CMS010, CMS011, CMS013, CMS014, CMS015, CMS018, CMS019, CMS020, CMS026, CMS028, CMS029, CMS030, CMS034, and CMS036 were found to be able to inhibit anti-SRBC antibody formation, having statistically significant difference from the saline group (P<0.05). Data detailed in Table 20 below.

TABLE 20

| Group | N | X ± SD (Unit) |
|---|---|---|
| CMS002 | 9 | 4 ± 1* |
| CMS003 | 9 | 2 ± 1* |
| CMS009 | 9 | 2 ± 1* |
| CMS010 | 10 | 10 ± 3* |
| CMS011 | 10 | 5 ± 3* |
| CMS013 | 10 | 7 ± 1* |
| CMS014 | 10 | 15 ± 6* |
| CMS015 | 9 | 13 ± 4* |
| CMS018 | 9 | 3 ± 1* |
| CMS019 | 9 | 12 ± 3* |
| CMS020 | 9 | 10 ± 3* |
| CMS021 | 9 | 57 ± 9*@ |
| CMS023 | 10 | 108 ± 21*@^ |
| CMS024 | 10 | 98 ± 6*@^ |
| CMS026 | 10 | 19 ± 6* |
| CMS027 | 10 | 99 ± 14*@^ |
| CMS028 | 10 | 18 ± 5* |
| CMS029 | 9 | 18 ± 7* |
| CMS030 | 9 | 19 ± 7* |
| CMS033 | 9 | 78 ± 12*@ |
| CMS034 | 10 | 20 ± 2* |
| CMS036 | 9 | 20 ± 6* |
| IFN-γ | 9 | 37 ± 10 |
| IL-2 | 10 | 71 ± 11* |
| Saline | 10 | 32 ± 7 |

*comparing to saline group P < 0.05
@comparing to IFN-γ group P < 0.05
^comparing to IL-2 group P < 0.05

6. The Effect of Peptides on the Phagocytotic Activity of Mononuclear Phagocyte

At 500 μg/kg/day, CMS003, CMS008, CMS020, CMS022, and CMS024 were found to be able to enhance the phagocytotic activity of mononuclear phagocyte, having statistically significant difference from the saline group (P<0.05). Among these peptides, CMS022 was found to have statistically significant difference from the IFN-γ group and IL-2 group (P<0.05) as shown in Table 21.

TABLE 21

| Group | N | X ± SD (phagocytic index) |
|---|---|---|
| CMS003 | 10 | 6.6 ± 0.7* |
| CMS008 | 10 | 6.5 ± 1.2* |
| CMS020 | 10 | 6.4 ± 0.6* |
| CMS022 | 10 | 7.4 ± 0.6*@^ |
| CMS024 | 10 | 6.4 ± 1.0* |
| IFN-γ | 10 | 6.4 ± 0.9* |
| IL-2 | 9 | 5.7 ± 0.8 |
| Saline | 10 | 5.1 ± 0.6 |

*comparing to saline group P < 0.05
@comparing to IFN-γ group P < 0.05
^comparing to IL-2 group P < 0.05

At 50 μg/kg/day, CMS019, CMS024, and CMS030 were found to be able to enhance the phagocytotic activity of mononuclear phagocyte, having statistically significant difference from the saline group (P<0.05). Among these peptides, CMS019 was found to have statistically significant difference from the IL-2 group (P<0.05) as shown in Table 22.

TABLE 22

| Group | N | X ± SD (phagocytic index) |
|---|---|---|
| CMS019 | 9 | 6.7 ± 0.9*^ |
| CMS024 | 8 | 6.6 ± 0.7* |
| CMS030 | 10 | 6.3 ± 0.5* |
| IFN-γ | 10 | 6.4 ± 0.9* |
| IL-2 | 9 | 5.7 ± 0.8 |
| Saline | 10 | 5.1 ± 0.6 |

*comparing to saline group P < 0.05
^comparing to IL-2 group P < 0.05

At 5 μg/kg/day, CMS003, CMS008, CMS009, CMS010, CMS011, CMS013, CMS016, CMS018, CMS019, and CMS035 were found to be able to enhance the phagocytotic activity of mononuclear phagocyte, having statistically significant difference from the saline group (P<0.05). Among these peptides, CMS003, CMS009, CMS010, CMS016, CMS019, and CMS035 were found to have statistically significant difference from the IL-2 group (P<0.05) as shown in Table 23.

TABLE 23

| Group | N | X ± SD (phagocytic index) |
|---|---|---|
| CMS003 | 9 | 6.9 ± 0.9*^ |
| CMS008 | 9 | 6.4 ± 0.5* |
| CMS009 | 9 | 6.9 ± 0.9*^ |
| CMS010 | 10 | 7.1 ± 0.7*^ |
| CMS011 | 10 | 6.4 ± 1.1* |
| CMS013 | 10 | 6.7 ± 0.2* |
| CMS016 | 9 | 6.9 ± 0.8*^ |
| CMS018 | 8 | 6.7 ± 1.2* |
| CMS019 | 8 | 6.8 ± 0.6*^ |
| CMS035 | 9 | 6.9 ± 0.9*^ |
| IFN-γ | 10 | 6.4 ± 0.9* |
| IL-2 | 9 | 5.7 ± 0.8 |
| Saline | 10 | 5.1 ± 0.6 |

*comparing to saline group P < 0.05
^comparing to IL-2 group P < 0.05

At 0.5 μg/kg/day, CMS024, CMS027, and CMS036 were found to be able to enhance the phagocytotic activity of mononuclear phagocyte, having statistically significant difference from the saline group (P<0.05). Among these peptides, CMS024 was found to have statistically significant difference from the IL-2 group (P<0.05) as shown in Table 24.

TABLE 24

| Group | N | X ± SD (phagocytotic index) |
|---|---|---|
| CMS024 | 10 | 6.7 ± 0.5*^ |
| CMS027 | 10 | 6.4 ± 0.6* |
| CMS036 | 9 | 6.2 ± 0.3* |
| IFN-γ | 10 | 6.4 ± 0.9* |
| IL-2 | 9 | 5.7 ± 0.8 |
| Saline | 10 | 5.1 ± 0.6 |

*comparing to saline group P < 0.05
^comparing to IL-2 group P < 0.05

7. The Effect of Peptides on the Weight of Immune Organ

At 500 μg/kg/day, CMS008, CMS010, CMS016, CMS019, CMS020, CMS022, CMS026, CMS027, CMS028, CMS029, CMS030, CMS032, CMS033, CMS034, CMS035, and CMS036 were found to be able to increase the weight of thymus gland, having statistically significant difference from the saline group (P<0.05). Among these peptides, CMS027 and CMS034 were found to have statistically significant difference from the IL-2 group (P<0.05). And, CMS008, CMS022, CMS029, CMS030, CMS032, CMS033, and CMS035 were also found to have statistically significant difference from both the IFN-γ group and IL-2 group (P<0.05) as shown in Table 25.

TABLE 25

| Group | N | X ± SD (%) |
|---|---|---|
| CMS008 | 8 | 0.21 ± 0.03*@^ |
| CMS010 | 10 | 0.19 ± 0.04* |
| CMS016 | 9 | 0.18 ± 0.05* |
| CMS019 | 10 | 0.19 ± 0.02* |
| CMS020 | 10 | 0.19 ± 0.04* |
| CMS022 | 9 | 0.26 ± 0.05*@^ |
| CMS026 | 10 | 0.20 ± 0.03*^ |
| CMS027 | 8 | 0.20 ± 0.03*^ |
| CMS028 | 10 | 0.19 ± 0.02* |
| CMS029 | 10 | 0.22 ± 0.04*@^ |
| CMS030 | 8 | 0.30 ± 0.03*@^ |
| CMS032 | 8 | 0.25 ± 0.03*@^ |
| CMS033 | 9 | 0.25 ± 0.04*@^ |
| CMS034 | 9 | 0.20 ± 0.05*^ |
| CMS035 | 10 | 0.21 ± 0.03*@^ |
| CMS036 | 9 | 0.18 ± 0.02* |
| IFN-γ | 10 | 0.15 ± 0.04 |
| IL-2 | 9 | 0.14 ± 0.03 |
| Saline | 9 | 0.12 ± 0.02 |

*comparing to saline group P < 0.05
@comparing to IFN-γ group P < 0.05
^comparing to IL-2 group P < 0.05

At 500 μg/kg/day, CMS019 was found to be able to increase the weight of spleen, with statistically significant difference from the saline control groups (P<0.05) as shown in Table 26. CMS001, CMS003, CMS007, CMS009, CMS011, CMS013, CMS014, CMS015, CMS021, CMS023, CMS024, CMS027, and CMS036 were found to be able to decrease the weight of spleen, with statistically significant difference from the saline control group (P<0.05). Data detailed in Table 26 below.

TABLE 26

| Group | N | X ± SD (%) |
|---|---|---|
| CMS001 | 10 | 0.43 ± 0.07* |
| CMS003 | 8 | 0.40 ± 0.04* |
| CMS007 | 9 | 0.32 ± 0.05* |
| CMS009 | 9 | 0.41 ± 0.03* |
| CMS011 | 9 | 0.41 ± 0.04* |
| CMS013 | 10 | 0.44 ± 0.07* |
| CMS014 | 10 | 0.40 ± 0.03* |
| CMS015 | 9 | 0.36 ± 0.07* |
| CMS019 | 9 | 0.63 ± 0.08* |
| CMS021 | 9 | 0.36 ± 0.04* |
| CMS023 | 9 | 0.36 ± 0.06* |
| CMS024 | 9 | 0.34 ± 0.05* |
| CMS027 | 10 | 0.37 ± 0.03* |
| CMS036 | 10 | 0.40 ± 0.03* |
| Saline | 10 | 0.53 ± 0.05 |

*comparing to saline group P < 0.05

At 50 μg/kg/day, CMS002, CMS008, CMS012, CMS014, CMS016, CMS018, CM019, CMS020, CMS022, CMS023, CMS024, CMS026, CMS027, CMS028, CMS029, CMS030, CMS032, CMS033, CMS034, and CMS036 were found to be able to increase the weight of thymus gland, having statistically significant difference from the saline group (P<0.05). Among these peptides, CMS034 was found to have statistically significant difference from the IL-2 group (P<0.05). And, CMS002, CMS008, CMS012, CMS014, CMS016, CMS018, CMS019, CMS020, CMS022, CMS023, CMS024, CMS026, CMS027, CMS030, CMS032, and CMS036 were also found to have statistically significant difference from both the IFN-γ group and IL-2 group (P<0.05) as shown in Table 27.

TABLE 27

| Group | N | X ± SD (%) |
|---|---|---|
| CMS002 | 10 | 0.21 ± 0.02*@^ |
| CMS008 | 10 | 0.20 ± 0.04*@^ |
| CMS012 | 10 | 0.26 ± 0.02*@^ |
| CMS014 | 10 | 0.21 ± 0.02*@^ |
| CMS016 | 10 | 0.20 ± 0.03*@^ |
| CMS018 | 10 | 0.23 ± 0.02*@^ |
| CMS019 | 10 | 0.20 ± 0.03*@^ |
| CMS020 | 10 | 0.27 ± 0.03*@^ |
| CMS022 | 10 | 0.30 ± 0.03*@^ |
| CMS023 | 10 | 0.20 ± 0.02*@^ |
| CMS024 | 10 | 0.27 ± 0.02*@^ |
| CMS026 | 10 | 0.27 ± 0.02*@^ |
| CMS027 | 8 | 0.21 ± 0.03*@^ |
| CMS028 | 10 | 0.18 ± 0.04* |
| CMS029 | 9 | 0.18 ± 0.05* |
| CMS030 | 10 | 0.25 ± 0.04*@^ |
| CMS032 | 10 | 0.27 ± 0.03*@^ |
| CMS033 | 9 | 0.18 ± 0.03* |
| CMS034 | 8 | 0.19 ± 0.04*^ |
| CMS036 | 9 | 0.22 ± 0.02*@^ |
| IFN-γ | 10 | 0.15 ± 0.04 |
| IL-2 | 9 | 0.14 ± 0.04 |
| Saline | 9 | 0.12 ± 0.02 |

*comparing to saline group P < 0.05
@comparing to IFN-γ group P < 0.05
^comparing to IL-2 group P < 0.05

At 50 μg/kg/day, CMS008, CMS010, and CMS029 were found to be able to decrease the weight of spleen, with statistically significant difference from the saline control group (P<0.05). Data detailed in Table 28 below.

TABLE 28

| Group | N | X ± SD (%) |
| --- | --- | --- |
| CMS008 | 10 | 0.39 ± 0.08* |
| CMS010 | 10 | 0.38 ± 0.05* |
| CMS029 | 10 | 0.42 ± 0.04* |
| IFN-γ | 10 | 0.50 ± 0.04 |
| IL-2 | 9 | 0.62 ± 0.07 |
| Saline | 9 | 0.53 ± 0.05 |

*comparing to saline group P < 0.05

At 5 μg/kg/day, CMS001, CMS002, CMS010, CMS011, CMS012, CMS013, CMS014, CMS015, CMS016, CMS018, CMS019, CMS020, CMS021, CMS022, CMS023, CMS024, CMS026, CMS028, CMS029, CMS030, CMS032, CMS033, CMS034, CMS 035 and CMS036 were found to be able to increase the weight of thymus gland, having statistically significant difference from the saline group (P<0.05). Among these peptides, CMS002, CMS014, CMS024, and CMS030 were found to have statistically significant difference from the IL-2 group (P<0.05). And, CMS010, CMS012, CMS018, CMS019, CMS020, CMS022, CMS026, CMS028, CMS032, CMS034, and CMS036 were also found to have statistically significant difference from both the IFN-γ group and IL-2 group (P<0.05) as shown in Table 29.

TABLE 29

| Group | N | X ± SD (%) |
| --- | --- | --- |
| CMS001 | 10 | 0.22 ± 0.05* |
| CMS002 | 9 | 0.24 ± 0.05*^ |
| CMS010 | 9 | 0.27 ± 0.05*@^ |
| CMS011 | 10 | 0.22 ± 0.04* |
| CMS012 | 10 | 0.27 ± 0.06*@^ |
| CMS013 | 10 | 0.21 ± 0.05* |
| CMS014 | 10 | 0.23 ± 0.06*^ |
| CMS015 | 9 | 0.20 ± 0.08* |
| CMS016 | 10 | 0.22 ± 0.06* |
| CMS018 | 10 | 0.24 ± 0.04*@^ |
| CMS019 | 10 | 0.24 ± 0.02*@^ |
| CMS020 | 10 | 0.24 ± 0.07*@^ |
| CMS021 | 9 | 0.20 ± 0.06* |
| CMS022 | 9 | 0.25 ± 0.04*@^ |
| CMS023 | 10 | 0.23 ± 0.06* |
| CMS024 | 9 | 0.23 ± 0.06*^ |
| CMS026 | 10 | 0.31 ± 0.05*@^ |
| CMS028 | 10 | 0.28 ± 0.06*@^ |
| CMS029 | 10 | 0.21 ± 0.03* |
| CMS030 | 10 | 0.23 ± 0.07*^ |
| CMS032 | 10 | 0.29 ± 0.04*@^ |
| CMS033 | 10 | 0.20 ± 0.02* |
| CMS034 | 9 | 0.27 ± 0.06*@^ |
| CMS035 | 10 | 0.21 ± 0.04* |
| CMS036 | 10 | 0.25 ± 0.04*@^ |
| IFN-γ | 10 | 0.15 ± 0.04 |
| IL-2 | 9 | 0.14 ± 0.04 |
| Saline | 9 | 0.12 ± 0.02 |

*comparing to saline group P < 0.05
@comparing to IFN-γ group P < 0.05
^comparing to IL-2 groupP < 0.05

At 5 μg/kg/day, CMS030 was found to be able to increase the weight of spleen, having statistically significant difference from the saline group (P<0.05). CMS015 was found to be able to decrease the weight of spleen, having statistically significant difference from the saline group (P<0.05). Data detailed in Table 30 below.

TABLE 30

| Group | N | X ± SD (%) |
| --- | --- | --- |
| CMS015 | 9 | 0.38 ± 0.15* |
| CMS030 | 10 | 0.64 ± 0.09* |
| Saline | 10 | 0.53 ± 0.05 |

*comparing to saline group P < 0.05

At 0.5 μg/kg/day, CMS002, CMS008, CMS010, CMS012, CMS014, CMS018, CMS020, CMS022, CMS026, CMS028, CMS030, and CMS032 were found to be able to increase the weight of the thymus gland, having statistically significant difference from the saline group (P<0.05). Among these peptides, CMS008 and CMS012 were found to have statistically significant difference from the IL-2 group (P<0.05). And, CMS002, CMS020, and CMS030 were also found to have statistically significant difference from both the IFN-γ group and IL-2 group (P<0.05) as shown in Table 31.

TABLE 31

| Group | N | X ± SD (%) |
| --- | --- | --- |
| CMS002 | 8 | 0.26 ± 0.06*@^ |
| CMS008 | 10 | 0.22 ± 0.07*^ |
| CMS010 | 9 | 0.21 ± 0.03*^ |
| CMS012 | 10 | 0.22 ± 0.06*^ |
| CMS014 | 10 | 0.20 ± 0.04* |
| CMS018 | 10 | 0.20 ± 0.03* |
| CMS020 | 9 | 0.23 ± 0.05*@^ |
| CMS022 | 10 | 0.21 ± 0.06* |
| CMS026 | 9 | 0.21 ± 0.05* |
| CMS028 | 10 | 0.20 ± 0.06* |
| CMS030 | 8 | 0.24 ± 0.05*@^ |
| CMS032 | 10 | 0.21 ± 0.06* |
| IFN-γ | 10 | 0.15 ± 0.04 |
| IL-2 | 9 | 0.14 ± 0.04 |
| Saline | 9 | 0.12 ± 0.02 |

*comparing to saline group P < 0.05
@comparing to IFN-γ group P < 0.05
^comparing to IL-2 groupP < 0.05

At 0.5 μg/kg/day, CMS020 was found to be able to increase the weight of spleen, having statistically significant difference from the saline group, IFN-γ group, and IL-2 group (P<0.05). CMS001 was found to be able to decrease the weight of spleen, having statistically significant difference from the saline group (P<0.05). Data detailed in Table 32 below.

TABLE 32

| Group | N | X ± SD (%) |
| --- | --- | --- |
| CMS001 | 10 | 0.40 ± 0.05* |
| CMS020 | 8 | 0.68 ± 0.09*@^ |
| Saline | 10 | 0.53 ± 0.05 |
| IFN-γ | 10 | 0.50 ± 0.04 |
| IL-2 | 10 | 0.62 ± 0.07 |

*comparing to saline group P < 0.05
@comparing to IFN-γ group P < 0.05
^comparing to IL-2 group P < 0.05

In summary, we found that peptides CMS001, CMS002, CMS003, CMS007, CMS008, CMS009, CMS010, CMS011, CMS012, CMS013, CMS014, CMS015, CMS016, CMS018, CMS019, CMS020, CMS021, CMS022, CMS023, CMS024, CMS026, CMS027, CMS028, CMS029, CMS030, CMS032, CMS033, CMS034, CMS035, and CMS036 have in vivo biological activities in the animal model tested.

II. The In Vivo Antiviral Effect of Peptides

In order to find out whether these peptides have possible therapeutic effect on viral infections, we used the animal model duck hepatitis B infection in this study to test out the in vivo effects of the above peptides on diseased animals.

Chongqing duck hepatitis B model was set up and treated with peptides by intraperitoneal injection (50 µg/kg/day, once per day) for 4 weeks. The serum level of DHBV DNA was analyzed by serum dot-blot hybridization. Lamivudine and normal saline treatment was used as positive and negative control respectively. The peptide CMS001 was found to be able to reduce the serum level of DHBV DNA at the 4th week of the treatment, having statistically significant difference from the saline control group ($p<0.05$). It is concluded that CMS001 at suitable dosage level can be used as a part, or on its own, for viral hepatitis infection management.

Materials and Methods

1. Peptides were custom synthesized by American Peptide Company, Inc., USA, from L-amino acids.

2. Animal Model[1]

One-day old Chongqing ducks were inoculated with 0.1 ml stock serum positive of Duck Hepatitis B Virus (DHBV) DNA ($5 \times 10^7$ copy/ml) by intraperitoneal injection. One week later, blood samples were collected from the external jugular vein and infection was confirmed by dot-blot hybridization with DHBV DNA probe labeled with digoxin[2]. The ducks were breed to 2 weeks old for entrance into the study.

3. Grouping and Treatment

DHBV infected ducks were randomized into the following groups:
   a) Negative control group (n=9): Normal saline was given 1 ml per duck by intraperitoneal injection, once per day.
   b) Lamivudine group (n=8): As positive control group. Lamivudine[4] was given 50 mg/kg/day by oral administration, once per day.
   c) Peptide group (n=9): 50 µg/kg/day peptide (adjusted to final volume of 0.5 to 1 ml with normal saline) was given once per day by intraperitoneal injection.

Treatment lasted for 4 weeks and observation continued for another one week after termination of treatment. 1 ml blood samples were drawn from the external jugular vein of the ducks on days 0, 7, 14, 21, 28, and 35 when treatment started. Sera of the blood samples were isolated immediately [3] and stored at −20° C. until analysis.

4. Serum DHBV DNA Level Determinations

DHBV DNA probe was fluorescent labeled according to the labeling kit protocol from the kit manufacturer (Amersham Pharmacia Biotech Co.). 40 µl duck sera were dot-blotted (1 duplicated dot per sample) onto nitro-cellulose membrane and hybridized with fluorescent-labeled DHBV DNA probe for quantitation [2]. After completion of hybridation, the blots were developed in CDP-Star fluorimetry reagent RPN3690 and scanned with Vuego Scan (Brisa-620st) scanner. ImageMaster TotalLab v1.11.lnk software was used for quantitative analysis of the blots. Statistical analysis was carried out according to the pair t-test with SPSS software.

Results

TABLE II.1

Serum DHBV DNA titer before and after treatment

| | DHBV DNA level (Mean ± Standard Deviation, $10^3$ units) | | | | | |
|---|---|---|---|---|---|---|
| | Day 0 | Day 7 | Day 14 | Day 21 | Day 28 | Day 35 |
| Normal saline | 26 ± 12 | 45 ± 31 | 49 ± 23 | 102 ± 66 | 60 ± 38 | 50 ± 43 |
| Lamivudine | 21 ± 9 | 6 ± 4* | 7 ± 6* | 8 ± 7* | 8 ± 5* | 20 ± 19 |
| CMS001 | 21 ± 18 | 11 ± 13 | 20 ± 18 | 14 ± 14 | 5 ± 3* | 18 ± 16 |

Pair t-test, comparing with day 0 of the same animals: *$P < 0.05$

The negative (normal saline) and positive (lamivudine) control group proved successful establishment of the hepatitis animal model. At 50 µg/kg/day, the peptide CMS001 was found to be able to decrease the serum DHBV DNA titre after 4 weeks of treatment, having statistically significant difference ($p<0.05$) from the before treatment value of the same animals. Upon termination of treatment, the serum DHBV DNA titre rebounced to a value with no statistical difference from that before treatment, showing that the effect of peptide CMS001 may be reversible and/or need longer treatment period for eradication of the virus.

Discussion

Duck hepatitis animal model[1] is an established experimental model for human hepatitis B pathogenesis studies and for the screening of hepatitis B therapeutic agents. In this study, CMS001 was found to be able to decrease the serum titre of DHBV DNA after 4 weeks of treatment, indicating that the peptide CMS001 at suitable dosage level and with suitable application scheme, can be useful on its own or in combination with other substances as an agent for human hepatitis B management.

In the present study, administration by intraperitoneal injection was tested, but this does not exclude the possible effectiveness of the peptide if administered via other alternative routes. The peptides may also be administered via intravenous injection, intramuscular injection, subcutaneous injection, and subcutaneous implantation, with or without delivery facilitating device such as liposome, sustain release protection etc. The peptide may also be administered in any form of oral administration like tablet, capsule, suspension, solution etc, in the usual form without modification or in slow release form, or with or without gastro-enteric protection. The peptide may further be applied in any form of topic application like ointment, cream, gel etc with or without transdermal facilitating device, or as inhalant of powder, dissolved, or as liposome protected form. The peptide may also be interpreted into its genetic sequence and cloned into an expression system, on its own or in combination with other peptide sequences, to generate a resulting peptide molecule to make use of the activity of the peptide as described in this report, with or without purification of the resulting peptide.

TABLE II.2

Peptides Effective for Hepatitis B

| CMS code | SEQ ID No. |
|---|---|
| CMS001 | 1 |

REFERENCES

1. Chen Yaxi, Guo shuhua, Zhang Dingfeng, et al. Foundation and application of Chongqing duck hepatitis B model. Chinese Journal of Hepatology. 1993; 1(2): 89-91
2. Chen Yaxi, Guo shuhua, Chen Xuehua. Preparation and application of DHBV DNA probe labeled with digoxin. Journal of Chongqing University of Medical Sciences. 1994; 19(4): 295-297
3. Tang Ni, Huang Ailong, Guo shuhua, et al. Systemic foundation and application of serological parameters of humoral immunity to duck hepatitis B virus. Chinese Journal of Hepatology. 2001; 9(1): 13-15
4. Chen Yaxi, Guo shuhua, Qi Zhenyuan, et al. An experimental study of lamivudine against duck hepatitis B virus in combination with famciclovir. Chinese Journal of Hepatology. 2001; 9(4): 209-211

III. Effect of Peptides on Nephritis

In order to find out whether these peptides have possible therapeutic effect on nephritis, we used the animal model rat Masugi nephritis in this study to test out the in vivo effects of the above peptides on diseased animals[3,4].

The objective of this study is to investigate the in vivo therapeutic effect of peptides on chronic glomerulonephritis. Masugi nephritis rat model was constructed by injecting rabbit anti-rat-renal-cortex IgG into heathy Sprague Dawley rats, and then treated immediately with intraperitoneal injection of peptides at 50 μg/kg/day, once per day for 3 weeks. Hydrocortisone was used as positive control. It was found that proteinurea, serum creatinine level, and splenic index of the rats treated with CMS014, CMS018, CMS030, and CMS036 were lowered compared with that of the control group, with statistical significance (p<0.05). Postmortum microscopic examination of the kidney showed that the therapeutic effect of these peptides was similar to hydrocortisone treatment. It is concluded that CMS014, CMS018, CMS030, and CMS036 may be used as a means for chronic nephritis management.

Materials

Sprague Dawley (SD) rats, male, weighing 120±20 g, were from Center of Experimental Animal, Guangzhou University of Traditional Chinese Medicine, and also from First Military Medical University. Chinchilla rabbits weighing 3 kg were from Center of Experimental Animal, Guangzhou University of Traditional Chinese Medicine.

Peptides, of L-amino acids origin, were custom synthesized by American Peptide Company, Inc, USA, and were diluted to 10 μg/ml in sterile normal saline. Hydrocortisone was from Yangzhou Pharmaceutical Factory, China.

Serum creatinine level determination kit from Shanghai Rongsheng Biological Technique Company, PR China.

Methods

1. Preparation of Rabbit Anti-Rat-Renal-Cortex Anti-Serum[1]:

20 healthy SD rats were anesthetized with intravenous injection of 3% sodium pentobarbital, 40 mg/kg. The aorta abdominalis was exposed and the kidneys were perfused with normal saline until clean of blood. The renal cortex was isolated, homogenized in 5 volumes of 0.01M Tris-HCl buffer, pH 8.1, and filtered through a 140-gauge stainless steel mesh. The filtrate was collected and mixed with either GIBCO-RRE complete or incomplete Freunds adjuvant in 1:1 and emulsified to obtain the working immunization solution.

10 healthy rabbits were immunized with the immunization solutions, first time with complete Freunds adjuvant and subsequently with the incomplete one. The antigen was injected hypodermally through 6 random points, 0.1 ml per point, once per 10 days. From $6^{th}$ week onwards, blood was collected from the auricular vein and the antibody titer was determined by the double diffusion method[2]. On the $8^{th}$ week after starting of immunization, the rabbits were anesthetized with intravenous injection of 3% sodium pentobarbital, 20 mg/kg, and blood was collected from the carotid artery. The anti-serum was then exuded and isolated.

Whole blood was collected from 15 healthy SD rats. The red blood cell was isolated and washed clean thrice with normal saline. The clean red blood cell was mixed with 250 ml rabbit anti-serum and incubated at 4° C. overnight. After incubation, the blood cell was removed by centrifugation and the supernatant was further inactivated at 56° C. for 30 minutes. After centrifugation to remove any precipitate, crude IgG was isolated and partially purified from the supernatant by precipitation with $(NH_4)_2SO_4$ thrice (50%, 33%, and then 33%)[5]. The crude IgG was redissolved in 125 ml double distilled water and dialysed clean of ammonium sulphate. The anti-rat-renal-cortex antibody titer was determined by the double diffusion method[2].

2. Induction of Rat Glomerulonephritis[5]:

0.25 ml priming solution (containing about 4 mg non-specific rabbit IgG with complete Freunds adjuvant) was injected intraperitoneally into healthy SD rats to prime the rats five days before induction. With the exception of the normal healthy control group that received normal saline, all groups were subsequently induced by intraperitoneal injection of 1 ml rabbit anti-rat-renal-cortex IgG prepared as described in section Method 1.

3. Grouping and Administration:

Male SD rats were randomized into groups of normal healthy control (normal), nephritis placebo treatment control (placebo), nephritis peptide treatment, and the nephritis hydrocortisone treatment control (hydrocortisone), 12 per group. Treatment started on the day of induction. Peptides 50 μg/kg/day, hydrocortisone 3.3 mg/kg/day, and normal saline was used as placebo, all administered intraperitoneally once per day and lasted for 3 weeks.

4. Parameters Monitored[4]:

(a) urine protein level: each rat was kept individually in one cage. Adequate drinking water was supplied. Urine was collected once per week, 24 hours per time. Protein content of the urine was determined by the Coomassie blue method.

(b) serum creatinine level: blood was collected after three weeks of treatment and serum creatinine level determination. The creatinine kit was provided by Shanghai Rongsheng Biological Technique Company.

(c) Spleen weight index: spleen weight index was determined by the following formula:

Spleen weight index=mean spleen weight÷mean body weight (d) Pathological microscopic examination of kidney: 6 heaviest kidneys were chosen from each group for pathological examination.

Statistical Analysis

Used t-test for inter-group comparisons, cut off set at p<0.05. For all groups, the two rats with lowest urinary protein levels were excluded from the statistical analysis.

Result

1. The Effect of Peptide Treatment on the Urine Protein Level

TABLE III.1

The effect of peptide treatment on urine protein level (unit: mg)

| Groups | n | Week 1 | Week 2 | Week 3 |
|---|---|---|---|---|
| CMS014 | 10 | 5.5 ± 4.0* | 6.3 ± 6.8* | 2.8 ± 1.9* |
| CMS018 | 10 | 7.0 ± 3.7* | 5.5 ± 7.9* | 3.3 ± 3.4* |
| CMS030 | 10 | 5.4 ± 3.4* | 9.5 ± 16.2 | 2.4 ± 1.5* |
| CMS036 | 10 | 7.9 ± 5.8* | 5.0 ± 7.1* | 1.3 ± 0.9* |
| hydrocortisone | 10 | 3.1 ± 2.0* | 7.5 ± 7.7 | 7.6 ± 7.1* |
| placebo | 10 | 22.9 ± 22 | 17.2 ± 14.5 | 20.2 ± 29.0 |
| normal | 9 | 1.7 ± 1.3* | 2.3 ± 1.1* | 0.4 ± 0.2* |

Comparing with placebo,
*p < 0.05

It was found that peptides CMS014, CMS018, CMS030, and CMS036 at 50 μg/kg/day once per day can lower the urine protein level of Masugi nephritis rat model, with statistically significant difference from the placebo treated control group, $p<0.05$. It was also noted that the growth rate of groups CMS014, CMS030, CMS036, and hydrocortisone have slower growth rate than normal. The growth rate of the hydrocortisone group decreased to such an extent that after the first week, the treatment dose has to be halved to avoid severe intolerance.

2. The Effect of Peptide Treatment on the Serum Creatinine Level

TABLE III.2

The influence of peptides on the serum creatinine level

| Groups | n | Serum creatinine level (μmol/L) |
|---|---|---|
| CMS014 | 10 | 159 ± 1 |
| CMS018 | 10 | 67 ± 1* |
| CMS030 | 10 | 93 ± 1* |
| CMS036 | 10 | 80 ± 1* |
| Placebo | 10 | 265 ± 212 |
| hydrocortisone | 10 | 239 ± 107 |
| normal | 9 | 80 ± 1* |

Comparing with nephritis rats receiving placebo treatment (placebo),
*p < 0.05

The serum creatinine level of Masugi nephritis rats receiving placebo treatment was much higher than that of the normal control group, showing that the renal function of the nephritis rats was abnormal. It was found that the peptides CMS014, CMS018, CMS030, and CMS036 at 50 μg/kg/day once per day were able to lower the level of serum creatinine, with statistically significant difference from the nephritis rats with placebo treatment.

3. The Effect of Peptides on the Spleen Indexes

TABLE III.3

The effect of peptides on the spleen index ($\times 10^{-3}$)

| Groups | n | spleen index |
|---|---|---|
| CMS014 | 10 | 3.6 ± 1.3* |
| CMS018 | 10 | 3.3 ± 0.8* |
| CMS030 | 10 | 3.0 ± 0.5* |
| CMS036 | 10 | 3.4 ± 0.8* |
| placebo | 10 | 4.8 ± 1.1 |
| hydrocortisone | 10 | 4.5 ± 1.4 |
| normal | 9 | 2.4 ± 0.1* |

Comparing with nephritis rats receiving placebo treatment (placebo),
*p < 0.05

The spleens of all induced rats were enlarged compared with normal rats, showing that the induction of nephritis was related to immune response. It was found that the peptides CMS014, CMS018, CMS030, and CMS036 at 50 μg/kg/day once per day were able to decrease the spleen index, with statistically significant difference from the group of nephritis rats receiving placebo treatment, $p<0.05$. This suggested that the peptides might exert their corrective effect against nephritis through immunosuppression mechanisms.

4. The Effects of Peptides on the Renal Pathological Microscopic Examination

Comparing with normal rats, the nephritis rats receiving placebo treatment (placebo group) showed signs of fibrous tissue formation in the glomerular capsule, hyperplasia of the glomerular epithelium, formation of crescents, dilation and congestion of glomerular capillaries, edema of the proximal tubule epithelium, and cast formation in the distal tubule and collecting duct. These pathological changes confirmed the successful induction of nephritis. It was observed that in the group CMS014, there was only one rat showed signs of fibrous tissue formation in the glomerular capsule and hyperplasia of the glomerular epithelium. Other parameters of the same rat, and other rats of the same group have essentially the same renal histology as normal rats. In the groups CMS018, CMS030, and CMS036, all pathological parameters of all rats were normal.

Conclusion

It is concluded that the peptides CMS014, CMS018, CMS030, and CMS036 at 50 μg/kg/day, once per day, administered intraperitoneally can have therapeutic effect on experimental Masugi nephritis rat model. Proteinurea, creatinine excretion, and renal histology of the treated rats were corrected by these peptides, with statistically significant difference from the control group receiving placebo treatment. These peptides may act through immunological mechanisms as indicated by their influence on the spleen weight index, but does not exclude the possibility of their actions via other mechanisms.

Discussion

The peptides CMS014, CMS018, CMS030, and CMS036 may be useful as a part, or on its own, in nephritis management in human. For example, the peptides may be used to correct proteinurea or to restore the excretary functions of nephritis patients. The peptides may also be used to prevent further kidney function impairment in nephritis patients. The peptides may be used on its own, in combinations of two or more peptides, or in combination with other pharmaceuticals or food supplements as a total course for nephritis management.

TABLE III.4

Peptides Effective for Nephritis

| CMS code | SEQ ID No. |
|---|---|
| CMS014 | 7 |
| CMS018 | 10 |
| CMS030 | 21 |
| CMS036 | 26 |

REFERENCES

1. SDA (State Drug Administration, P.R. China). The guideline of preclinical researches of new drugs. 1994, the 1st edition, Page 96

2. Xu Shuyun, et al. The methodology of pharmacological experiment, the People's Sanitation Publishing Company, Beijing, the 2nd edition, 1991:1071.
3. Chen Qi, et al. The methodology of pharmacological researches of traditional Chinese medicine, the People's Sanitation Publishing Company, Beijing, the 1st edition. 1993:390.
4. Du Guanhua. The guideline for pharmacological experiment—the discovery and pharmacological evaluation of new drugs, Science Publishing Company, Beijing, the 1st edition, 2001:598.
5. Wang Shuxian. Nephrology, the People's Sanitation Publishing Company, Beijing, the 11th edition, 1987:244.

IV. Effect of CMS Peptides on Cancer

In order to find out whether these peptides have possible therapeutic on cancer, we used various standard animal cancer models in this study to test out the biological effects of the above peptides on diseased animals.

Materials

1. Experimental Animals

BALB/c mice, $C_{57}BL/6$ mice, and DBA/2 mice, weighing 18-22 g, from China Medical Science Institute, PR China.

2. Cell Lines

Mouse sarcoma $S_{180}$ cells, $B_{16}$ cells, and $L_{1210}$ cells, from Cancer Research Department, China Medical Science Institute.

YAC-1 cells, as gift from Prof Yao Zhi, Tianjin Medical University.

3. Main Drug and Reagent

The peptides used in this study were custom manufactured by American Peptide Company, Inc., USA.

Fetal bovine serum, RPMI-1640 cell culture medium, from Gibco, USA.

MTT, ConA, from Sigma, USA.

Recombinant mouse interferon-γ (rmIFN-γ), from Beijing Biotech Inc., PR China.

Recombinant human interleukin-2 (rhIL-2), from Shanghai Huaxin Biotech Inc., PR China.

Lymphocyte separation solution, from Research Institute of Hematologic Disease, National Institute of Medical Science, PR China Cyclophosphamide, from The 12th pharmaceutical factory of Shanghai, PR China.

II. METHODS

1. Administration of Test Substance

Intraperitoneal injection, once per day. With the exception of cyclophosphamide group, all groups started treatment 5 days before transplanting the cancer cells. The cyclophosphamide groups were treated on the next day after transplanting the cancer cells. Treatment of all groups with testing substance lasted for 30 days or until the animal died unless otherwise specified.

2. The Effect of Peptides on the Growth Rate of Transplanted $S_{180}$ Sarcoma Cells in BALB/c Mice, and that on the Immunological Function of the Host BALB/c mice were randomized into peptide group, cyclophosphamide group, rmIFN-γ group, rhIL-2 group, and saline group, 20 animals per group.

Stock $S_{180}$ sarcoma cells were incubated in DMEM/F12 medium supplemented with 10% fetal bovine serum, 37° C., 5% $CO_2$ for 72 hrs, then washed 3-4 times with Hank's solution at room temperature. Adjust the cell concentration to $1-2\times10^9$ per liter with Hank's solution. 0.2 ml of cell suspension was implanted to several BALB/c mice through the armpit for 10-12 days. The mice were killed by cervical vertebra dislocation. Vigorously growing and non-disrupted tumor masses were harvested and washed clean with sterile saline. The tissue was dispersed in saline to a homogenous cell suspension, in a ratio of 1 g tissue to 4 ml saline. The sarcoma bearing mice model was prepared with an injection of 0.2 ml cell suspension through the armpit [1]. Administration of test substance treatment started as described in section Method 1.

2.1 The effect of peptides on the phagocytotic function of mononuclear phagocyte in mice with $S_{180}$ sarcoma [2,3] was analyzed by injecting mice from the tail vein with 0.1 ml/10 g body weight of Indian ink (1:5 dilution with normal saline) on the second day after the last test substance administration. At one minute and five minutes after the injection, 20 μl blood was obtained from the eye canthus with heparinised tubing. The blood was mixed with 2 ml 0.1% w/v $Na_2CO_3$ and then $OD_{680nm}$ obtained. The outline clear index K was calculated by the following formula:

$$K=(\lg A_1-\lg A_2)\div(t2-t1)$$

Key:
A1: $OD_{680}$ nm at first minute
A2: $OD_{680}$ nm at fifth minute
t2: 5 minutes
t2: 1 minute After the phagocytosis index study, the mice were killed by cervical vertebra dislocation. The liver, spleen, and cancer tissue were dissected, blotted dry, and weighed.

1. The phagocytosis index α was calculated as below:

$$\alpha=(\sqrt[3]{K})\times(W\div W_{LS})$$

key:
W: body weight
$W_{LS}$: weight of liver plus spleen 2.2 The tumor growth inhibition index was calculated according to the following formula:

Tumor growth inhibition index=(mean tumor weight of control group−mean tumor weight of treatment group)÷mean tumor weight of control group 3. The Effect of Peptides on the Survival of BALB/c Mice with Transplanted Ascitic Fluid Type Liver Cancer $H_{22}$ BALB/c mice were randomly grouped into peptide group, cyclophosphamide group, rmIFN-γ group, rhIL-2 group and saline group, 20 animals per group.

Stock $H_{22}$ cells were incubated in DMEM/F12 medium supplemented with 10% fetal bovine serum, 37° C./5% $CO_2$ for 72 hrs, then washed 3-4 times with Hank's solution at room temperature. Adjust cell concentration to $1-2\times10^9$ per liter with Hank's solution. 0.2 ml of the cell suspension was implanted to the abdominal cavity of several BALB/c mice for 6-8 days [1]. The mice were killed by cervical vertebra dislocation. Ascitic fluid of the mice was collected asceptically and the cell concentration adjusted to $1\times10^6$ per ml with Hank's solution. 0.2 ml of the cell suspension was implanted into the abdominal cavity of healthy mice to generate the $H_{22}$ carrying mouse model for ascitic fluid type liver cancer. Administration of test substance started as described in section Method 1. Survival data of the mice was recorded. If the animal survived longer than the experiment, the survival days was recorded as the duration of the experiment. Mean survival day was obtained by the Kaplan-meier method in the Survival option of the SPSS software. The survival index was calculated according to the following formula:

Survival index=(mean survival days in treatment group−mean survival days of control group)÷mean survival days of control group×100%

4. The Effect of Peptides on the Cellular Immunity of BALB/c Mice with Transplanted Ascitic Fluid Type Liver Cancer $H_{22}$ 4.1 Preparation of Spleen Cell Suspension[1,4]

Healthy BALB/c mice were randomized into peptide group, rmIFN-γ group, rhIL-2 group, and saline group, 15 mice per group, and prepared into $H_{22}$ carrying mice model as described in section Method 3. After implantation of the cancer cells, the test substances were administered for 15 days, the mice were killed by cervical dislocation. The spleen was isolated aseptically and manually dispersed in cold D-Hank's solution using an injection needle. The dispersed cell suspension was further sieved through a 100-gauge 150 μm diameter stainless steel sieve. After centrifugation at 200 g for 10 minutes, the supernatant was discarded. The cell pellet was re-suspended in 10 volume of Tris-$NH_4Cl$ buffer and then kept standing still for 10 minutes at room temperature. The suspended cells were collected by centrifugation at 150 g for 10 minutes. The cells were washed 2-4 times with cold D-Hank's solution by re-suspending and collecting by centrifugation with condition as described above. The washed cells were then diluted to the desired cell densities by RPMI-1640 culture medium, containing 10% fetal bovine serum.

4.2 The Effect of Peptides on the T Lymphocyte Transformation in Mice with Ascitic Fluid Type Liver Cancer $H_{22}$[1,4]

Spleen cells of density 1×10⁶/ml were placed onto a 96 wells cell culture plate, 100 μl/well, three parallel wells each of the assay sample and control sample per mouse. To the assay wells, 100 μl/well ConA of 100 μg/ml in RPMI-1640 was added, and 100 μl/well plain RPMI-1640 was used for the controls. The cells were incubated for 66 hrs at 37° C., 5% $CO_2$. The cells were then pelleted by centrifugation at 150 g for 10 minutes. The supernatant was collected and stored at −20° C. for cytokines IL-2 and IFN determination.

50 μl/well MTT of 1 mg/ml in RPMI-1640 was added to the cell pellet and the cells re-suspended by shaking for 2 minutes. The incubation was continued for 4 hours. The supernatant was discarded after centrifugation at 150 g for 10 minutes. 120 μl 40 mM HCl-2-propanol was added to the cell pellet and shaken for 3 minutes. Use an ELISA reader to obtain $OD_{570}$ nm of each well referenced at 630 nm.

Each mouse formed three assay wells and three control wells. The Stimulation Index (SI) of each mouse was obtained by first deriving the average OD of the three parallel wells, then dividing the value of the assay wells by the control wells.

4.3 The Effect of Peptides on the NK Cell Activity in Mice with Ascitic Fluid Type Liver Cancer $H_{22}$[5,6]

Mice spleen cells were prepared to 4×10⁶/ml as described in section 4.1 above. Target cells YAC-1 were brought to log phase and adjusted to 1×10⁵/ml. Using a 96 wells cell culture plate, 100 μl mouse spleen cells and 100 μl culture medium were added to the control well containing only the spleen cells; 100 μl target cells and 100 μl culture medium were added to the control well containing only target cells; 100 μl mouse spleen cells and 100 μl target cells were added to the NK activity assay well. Three parallel sets of the above were prepared per mouse. After that, the 96 wells cell culture plates were incubated for 4 hrs at 37° C., 5% $CO_2$.

Samples were centrifuged at 150 g for 10 minutes to collect the cells. The supernatant was discarded and 50 μl/well MTT of 1 mg/ml was added. The reaction-mixture was then shaken for 2 minutes, and incubated at 37° C., 5% $CO_2$ for 4 hours. The supernatant was discarded after centrifugation at 150 g for 10 minutes. 120 μl 40 mM HCl-2-propanol was added and shaken for 3 minutes. An ELISA reader was used to obtain $OD_{570nm}$ of each well referenced at 630 nm.

Each mouse has 9 wells: three spleen cells only control, three target cells only control, and three assay wells with both spleen and target cells. The NK cell activity index of each mouse was obtained by first deriving the average OD of the three parallel wells of each combination, then applying this average OD to the following formula:

NK cell activity index=[1−(average OD of spleen and target cell well−average OD of spleen cell only well)÷(average OD of target cell only well)]×100%

5. The Effect of Peptides on the Survival of DBA/2 Mice with Transplanted $L_{1210}$ Leukemia DBA/2 mice, 6-8 weeks old, were randomized into peptide group, cyclophosphamide group, rmIFN-γ group, rhIL-2 group, and saline group, 20 animals per group.

Stock $L_{1210}$ cells were incubated in DMEM/F12 medium supplemented with 10% fetal bovine serum, 37° C./5% $CO_2$ for 72 hrs, then washed 3-4 times with Hank's solution, and adjusted to 1×10⁵ cells per liter. 0.1 ml of the cell suspension was implanted into the abdominal cavity of several healthy DBA mice for 6-8 days. The mice were then killed by cervical vertebra dislocation and their ascitic fluid collected aseptically. The cell concentration of the collected ascitic fluid was adjusted to 1×10⁵ per ml with Hank's solution. 0.1 ml of the cell suspension was implanted into each of the testing animal and the survival data of the animals recorded. Treatment started in the testing animals as described in section Method 1. Mean survival day was obtained by the Kaplan-meier method in the Survival option of the SPSS software. If the animal survived longer than the experiment, the survival days was entered as the duration of the experiment. The survival index was calculated according to the following formula:

Survival index=(mean survival days of treatment group−mean survival days of control group)÷mean survival days of control group 6. The Effect of Peptides on the Humoral Immunity of $C_{57}BL/6$ Mice Bearing Transplanted $B_{16}$ Melanoma, and that on the Metastatic Potential of the Inoculated Melanoma Cells $C_{57}BL/6$ mice, 6-8 weeks old, body weight 18-22 g, were randomized into peptide group, cyclophosphamide group, rmIFN-γ group, rhIL-2 group, and saline group, 20 animals per group.

Stock $B_{16}$ mouse melanoma cells were incubated in DMEM/F12 medium supplemented with 10% fetal bovine serum, 37° C./5% $CO_2$ for 72 hrs, then washed 3-4 times with Hank's solution. The cell concentration was adjusted to 1×10⁵ per ml with Hank's solution and 0.1 ml of the cell suspension was injected via the tail vein into the testing mice to generate the $B_{16}$ melanoma bearing animal model [7,8]. Treatment with test substance started as described in section Method 1.

6.1 The Effect of Peptides on the Humoral Immunity of $C_{57}BL/6$ Mice Bearing Transplanted $B_{16}$ Melanoma[9]

Sheep red blood cells (SRBC) were prepared by collecting blood from the cervical vein and put into a sterile flask with glass beads. The flask was shaken for 3 minutes and the blood then mixed with Alsever solution (glucose 2.05 g, NaCl 0.4 g, Sodium Citrate 0.8 g, adjust to 100 ml with distilled water) and stored at 4° C. Immediately before use, samples were centrifuged at 130 g, 5 minutes to collect the SRBC. The cells were washed two times by re-suspension and centrifugation in normal saline. Then the cell pellet was collected by centrifugation at 180 g for 10 minutes and re-suspended in saline to make the final working SRBC suspension, 2%.

Complement was prepared by adding 10 volumes of fresh Cavy serum into one volume centrifuge packed SRBC, and then gently shaken for 30 minutes at 4° C. The SRBC was removed by centrifugation at 200 g for 10 minutes. 10 volumes of normal saline were added to obtain the working complement solution.

On the testing animals, on the 27$^{th}$ date of test substance treatment, 0.2 ml of the working SRBC cell suspension was injected into each animal to raise antibody. On the day after the last test substance administration, blood was collected from the eye canthus and left at room temperature for one hour for serum exudation. After centrifugation at 200 g for 10 minutes, the collected serum was diluted by 500 times with normal saline.

To 1 ml diluted mouse serum of each mouse, 0.5 ml SRBC suspension was added. Ice cold. Then 1 ml working complement solution was added and incubated at 37° C. water bath for 10 minutes. Reactions were terminated by ice cold. Samples were then centrifuged at 200 g for 10 minutes to obtain the supernatant.

To 1 ml of this supernatant, 3 ml Drabkin solution was added and left at room temperature for 10 minutes. $OD_{540nm}$ was obtained.

Reference $OD_{540nm}$ was obtained by mixing 0.25 ml SRBC suspension with Drabkin solution to 4 ml and placed at room temperature for 10 minutes before $OD_{540nm}$ was taken.

Hemolysis index=($OD_{540nm}$ of test sample÷reference $OD_{540nm}$)×500

6.2 After the humoral immunity study, the mice were killed by cervical vertebra dislocation. Postmortem examination of the animals was performed. The pathological changes were recorded, and the numbers of melanoma lung metastasis foci were counted.

Results

1. The Effect of Peptide on the Cellular Phagocytosis in BALB/c Mice with Transplanted $S_{180}$ Sarcoma (Method 2.1)

TABLE IV.1

The effect of peptide on the phagocytosis index of BALB/c mice with transplanted $S_{180}$ sarcoma

| Group | Dose | N | Phagocytosis index |
|---|---|---|---|
| CMS001 | 50 µg/kg | 20 | 6.24 ± 0.33*^ |
| CMS001 | 5 µg/kg | 19 | 6.67 ± 0.43*^ |
| CMS034 | 5 µg/kg | 19 | 6.20 ± 0.44*^ |
| CMS034 | 0.5 µg/kg | 20 | 6.35 ± 1.02* |
| IL-2 | 3 × 10$^5$ IU/kg | 19 | 6.96 ± 1.37* |
| IFN-γ | 3 × 10$^5$ IU/kg | 17 | 5.45 ± 0.71 |
| Cyclo-phosphamide | 20 mg/kg | 19 | 5.92 ± 2.47 |
| Saline | 0.5 ml | 19 | 5.38 ± 0.85 |

*comparing to saline, P < 0.05
^comparing to rmIFN-γ, P < 0.05

CMS001 at 50 µg/kg/day and 5 µg/kg/day, and CMS034 at 5 µg/kg/day and 0.5 µg/kg/day were found to be able to increase the phagocytosis index, having statistically significant difference from the saline group.

2. The Effect of Peptide on the Growth Rate of Transplanted $S_{180}$ Sarcoma in BALB/c Mice (Method 2.2)

TABLE IV.2

The effect of peptide on transplanted S180 tumor growth

| Group | Dose | N | Tumor weight (g) | Tumor inhibition index (%) |
|---|---|---|---|---|
| CMS010 | 500 µg/kg | 20 | 0.67 ± 0.35* | 48.4 |
| CMS034 | 0.5 µg/kg | 20 | 0.83 ± 0.48* | 35.9 |
| CMS035 | 5 µg/kg | 20 | 0.71 ± 0.37* | 44.6 |
| IL-2 | 3 × 10$^5$ IU/kg | 20 | 0.69 ± 0.37* | 46.2 |
| IFN-γ | 3 × 10$^5$ IU/kg | 18 | 0.96 ± 0.45 | 25.3 |
| cyclo-phosphamide | 20 mg/kg | 20 | 0.68 ± 0.32* | 47.3 |
| Saline | 0.5 ml | 20 | 1.29 ± 0.50 | |

*comparing to saline group, P < 0.05

CMS010 at 500 µg/kg/day, CMS034 at 0.5 µg/day, and CMS035 at 5 µg/kg/day were found to be able to reduce the growth of the transplanted $S_{180}$ sarcoma, having statistically significant difference from the saline group (P<0.05).

3. The Effect of Peptide on the Survival of BALB/c Mice with Transplanted Ascitic Fluid Type Liver Cancer $H_{22}$ (Method 3)

TABLE IV.3

The effect of peptide on the survival index of BALB/c mice with transplanted ascitic fluid type liver cancer H22

| Group | Dose | N | Survival days | Survival index (%) |
|---|---|---|---|---|
| CMS008 | 5 µg/kg | 20 | 50.7 ± 20.9*^& | 67.8 |
| CMS011 | 5 µg/kg | 20 | 36.4 ± 22.2*^& | 60.2 |
| CMS024 | 50 µg/kg | 20 | 36.3 ± 12.7*^&$ | 38.4 |
| CMS024 | 5 µg/kg | 19 | 40.6 ± 14.6*^&$ | 54.8 |
| CMS024 | 0.5 µg/kg | 19 | 46.4 ± 14.8*^&$ | 76.9 |
| CMS032 | 0.5 µg/kg | 20 | 42.8 ± 12.2*^&$ | 63.3 |
| rhIL-2 | 3 × 10$^5$ IU/kg | 18 | 13.6 ± 0.5 | |
| rmIFN-γ | 3 × 10$^5$ IU/kg | 20 | 27.8 ± 7.5 | 6.1 |
| Cyclo-phosphamide | 20 mg/kg | 20 | 24.7 ± 10.2 | |
| Saline | 0.5 ml | 19 | 26.2 ± 6.8 | |

*comparing to saline, P < 0.05
^comparing to rmIFN-γ, P < 0.05
&comparing to rhIL-2, P < 0.05
$comparing to cyclophosphamide, P < 0.05

CMS008 at 5 µg/kg/day, CMS011 at 5 µg/kg/day, CMS024 at 50 µg/kg/day, CMS024 at 0.5 µg/kg/day, and CMS032 at 0.5 µg/kg/day were found to be able to prolong the survival of BALB/c mice with transplanted $H_{22}$ ascitic fluid type liver cancer, having statistically significant difference from the saline group (P<0.05). It was also observed that in the group CMS024 0.5 µg/kg/day, more than 30% (n=6) of the mice could survive longer than 90 days (two months after the experiment ended). Postmortem examination of the mice did not show sign of tumor establishment. CMS024 at 0.5 µg/kg/day therefore may interfere with the growth of the transplanted $H_{22}$ by interfering with its establishment or inducing the complete healing of the established cancer.

4. The Effect of Peptide on T Lymphocyte Transformation in BALB/c Mice with Transplanted Ascitic Fluid Type Liver Cancer $H_{22}$ (Method 4.2)

TABLE IV.4

The effect of peptide on T lymphocyte transformation

| Group | Dose | N | Stimulation index |
| --- | --- | --- | --- |
| CMS010 | 500 µg/kg | 20 | 1.45 ± 0.21*$ |
| CMS019 | 0.5 µg/kg | 19 | 1.50 ± 0.19*$ |
| CMS024 | 0.5 µg/kg | 19 | 1.46 ± 0.19*$ |
| CMS024 | 5 µg/kg | 20 | 1.45 ± 0.21*$ |
| CMS034 | 0.5 µg/kg | 20 | 1.37 ± 0.10*$ |
| CMS035 | 0.5 µg/kg | 20 | 1.40 ± 0.13*$ |
| CMS035 | 5 µg/kg | 20 | 1.46 ± 0.16*$ |
| rhIL-2 | 3 × 10⁵ IU/kg | 19 | 1.46 ± 0.21* |
| rmIFN-γ | 3 × 10⁵ IU/kg | 18 | 1.27 ± 0.14 |
| Cyclo-phosphamide | 20 mg/kg | 19 | 1.01 ± 0.23* |
| Saline | 0.5 ml | 20 | 1.25 ± 0.07 |

*comparing to saline, $P < 0.05$
$comparing to cyclophosphamide, $P < 0.05$

CMS010 at 500 µg/kg/day, CMS019 at 0.5 µg/kg/day, CMS024 at 0.5 µg/kg/day and 5 µg/kg/day, CMS034 at 0.5 µg/kg/day and CMS035 at 0.5 µg/kg/day and 5 µg/kg/day were found to be able to increase the stimulation index of T-lymphocyte, having statistically significant difference from the saline group (P<0.05).

5. The Effect of Peptide on the NK Cell Activity in BALB/c Mice with Transplanted Ascitic Fluid Type Liver Cancer $H_{22}$ (Method 4.3)

TABLE IV.5

The effect of peptide on the NK cell cytotoxic activity index

| Group | Dose | N | NK activity index(%) |
| --- | --- | --- | --- |
| CMS003 | 500 µg/kg | 17 | 37.9 ± 14.5*^$ |
| CMS014 | 0.5 µg/kg | 17 | 40.7 ± 19.7*$ |
| CMS024 | 0.5 µg/kg | 18 | 39.3 ± 18.7*$ |
| CMS024 | 5 µg/kg | 20 | 34.9 ± 12.1*^$ |
| CMS024 | 50 µg/kg | 20 | 43.6 ± 13.9*^$& |
| CMS032 | 5 µg/kg | 20 | 52.6 ± 12.5*^$& |
| CMS032 | 50 µg/kg | 19 | 41.0 ± 18.7*^$& |
| CMS034 | 50 µg/kg | 20 | 57.3 ± 17.9*^$& |
| IL-2 | 3 × 10⁵ IU/kg | 19 | 26.0 ± 9.0 |
| IFN-γ | 3 × 10⁵ IU/kg | 18 | 20.9 ± 3.3 |
| Cyclo-phosPhamide | 20 mg/kg | 19 | 16.5 ± 7.2* |
| Saline | 0.5 ml | 20 | 24.0 ± 8.2 |

*as compared with saline, $P < 0.05$.
^as compared with IFN-γ, $P < 0.05$.
&as compared with IL-2, $P < 0.05$.
$as compared with cyclophosphamide, $P < 0.05$ CMS003 at 500 µg/kg/day, CMS014 at 0.5 µg/kg/day, CMS024 at 0.5 µg/kg/day, 5 µg/kg/day, and 50 µg/kg/day, CMS032 at 5 µg/kg/day and 50 µg/kg/day and CMS034 at 50 µg/kg/day were found to be able to increase the NK cell cytotoxic activity in the testing animal model, having statistically significant difference from the saline group (P<0.05).

6. The Effect of Peptide on the Survival of DBA/2 Mice with Transplanted $L_{1210}$ Leukemia (Method 5)

TABLE IV.6

The effect of peptide on the survival index of testing animals

| Group | Dose | N | Survival days | Survival index (%) |
| --- | --- | --- | --- | --- |
| CMS019 | 0.5 µg/kg | 20 | 21.1 ± 5.8* | 26.8 |
| CMS035 | 0.5 µg/kg | 20 | 29.3 ± 15.4* | 76.1 |
| IL-2 | 3 × 10⁵ IU/kg | 20 | 32.0 ± 13.7* | 92.3 |
| IFN-γ | 3 × 10⁵ IU/kg | 20 | 15.6 ± 2.2 | |
| Cyclophosphamide | 20 mg/kg | 20 | 24.0 ± 5.3* | 44.2 |
| Saline | 0.5 ml | 21 | 16.6 ± 5.6 | |

*comparing to saline group, $P < 0.05$

CMS019 at 0.5 µg/kg/day and CMS035 at 0.5 µg/kg/day were found to be able to prolong the survival of DBA/2 mice with transplanted L1210 leukemia, having statistically significant difference from the saline group (P<0.05).

7. The Effect of Peptide on the Humoral Immunity of $C_{57}$BL/6 Mice with Transplanted $B_{16}$ Melanoma (Method 6.1)

TABLE IV.7

The effect of peptide on the hemolysis index of C57BL/6 mice with transplanted B16 melanoma

| Group | Dose | N | Hemolysis index |
| --- | --- | --- | --- |
| CMS001 | 0.5 µg/kg | 20 | 51.0 ± 16.2*$ |
| CMS001 | 5 µg/kg | 20 | 41.3 ± 17.7*$ |
| CMS001 | 50 µg/kg | 19 | 45.0 ± 31.9*$ |
| CMS001 | 500 µg/kg | 20 | 36.0 ± 10.2*$ |
| CMS003 | 0.5 µg/kg | 20 | 61.6 ± 26.9*$ |
| CMS003 | 5 µg/kg | 20 | 37.2 ± 15.9*$ |
| CMS003 | 50 µg/kg | 20 | 38.7 ± 13.5*$ |
| CMS003 | 500 µg/kg | 20 | 35.9 ± 13.0*$ |
| CMS008 | 0.5 µg/kg | 19 | 42.7 ± 18.4*$ |
| CMS008 | 5 µg/kg | 20 | 38.9 ± 12.0*$ |
| CMS008 | 50 µg/kg | 20 | 37.1 ± 16.7*$ |
| CMS008 | 500 µg/kg | 20 | 50.1 ± 17.8*$ |
| CMS010 | 0.5 µg/kg | 18 | 34.9 ± 10.5*$ |
| CMS010 | 5 µg/kg | 20 | 51.0 ± 14.6*$ |
| CMS010 | 50 µg/kg | 20 | 39.6 ± 7.7*$ |
| CMS010 | 500 µg/kg | 20 | 50.1 ± 16.7*$ |
| CMS011 | 0.5 µg/kg | 20 | 32.0 ± 14.7* |
| CMS011 | 500 µg/kg | 20 | 34.4 ± 19.4* |
| CMS016 | 500 µg/kg | 20 | 43.3 ± 29.9* |
| CMS019 | 0.5 µg/kg | 20 | 42.0 ± 12.0*$ |
| CMS019 | 5 µg/kg | 20 | 35.4 ± 15.1* |
| CMS019 | 50 µg/kg | 20 | 28.3 ± 7.6* |
| CMS024 | 0.5 µg/kg | 20 | 43.0 ± 10.7*$ |
| CMS024 | 5 µg/kg | 20 | 42.2 ± 11.8*$ |
| CMS024 | 50 µg/kg | 20 | 27.8 ± 9.1* |
| CMS024 | 500 µg/kg | 18 | 30.1 ± 10.0* |
| CMS034 | 0.5 µg/kg | 18 | 50.8 ± 18.4*$ |
| CMS034 | 5 µg/kg | 19 | 43.0 ± 11.7*$ |
| CMS034 | 50 µg/kg | 20 | 30.2 ± 10.9* |
| CMS035 | 5 µg/kg | 20 | 38.9 ± 21.2*$ |
| CMS035 | 50 µg/kg | 20 | 44.7 ± 22.7*$ |
| CMS035 | 500 µg/kg | 19 | 40.5 ± 25.8* |
| rhIL-2 | 3 × 10⁵ IU/kg | 19 | 49.3 ± 24.7* |
| rmIFN-γ | 3 × 10⁵ IU/kg | 19 | 60.5 ± 17.4* |
| Cyclo-phosphamide | 20 mg/kg | 19 | 20.7 ± 19.1 |
| Saline | 0.5 ml | 20 | 19.0 ± 9.1 |

*comparing to saline, $P < 0.05$
^comparing to rmIFN-γ, $P < 0.05$
&comparing to rhIL-2, $P < 0.05$
$comparing to cyclophosphamide, $P < 0.05$ CMS001, CMS003, CMS008, CMS010, CMS011, CMS016, CMS019, CMS024, CMS034, and CMS035 were found to be able to enhance the humoral response (increase in hemolysis index) of $C_{57}BL/6$ mice with transplanted $B_{16}$ melanoma at dosages as shown on Table IV.7, having statistically significant difference from the saline group ($P<0.05$).

8. The Effect of Peptide on the Survival of Inoculated B16 Melanoma Cells in $C_{57}BL/6$ Mice (Method 6.2)

Postmortum examination of animals after the ending of test substance treatment did not show any sign of existence of B16 metastatic foci in the lung of mice treated with CMS008 at 0.5 µg/kg/day, 5 µg/kg/day, and 50 µg/kg/day, and CMS016 at 5 µg/kg/day and 500 µg/kg/day.

III. CONCLUSION

In compliance with the Preclinical New Drug Research Guidelines issued by Branch of Drug Administration, Department of Health, PR China in 1993, the effects of peptide on mice with transplanted cancer cells was studied. It was concluded that 1. CMS010, CMS034, and CMS035 at suitable dosage could significantly inhibit the development of transplanted $S_{180}$ sarcoma in mice;
2. CMS001 and CMS034 at suitable dosage could enhance the phagocytotic immune activities of mice transplanted with $S_{180}$ sarcoma;
3. CMS008, CMS011, CMS024, and CMS032 at suitable dosage could prolong the survival of mice transplanted with ascitic fluid type liver cancer H22;
4. CMS010, CMS019, CMS024, CMS034, and CMS035 at suitable dosage could enhance T lymphocyte transformation in mice transplanted with ascitic fluid type liver cancer H22;
5. CMS003, CMS014, CMS024, CMS032, and CMS034 at suitable dosage could increase the NK cell cytotoxic activity of mice transplanted with ascitic fluid type liver cancer H22;
6. CMS019 and CMS035 at suitable dosage could prolong the survival of mice transplanted with L1210 leukemia;
7. CMS008 and CMS016 at suitable dosage could inhibit the development of transplanted B16 melanoma in mice;
8. CMS001, CMS003, CMS008, CMS010, CMS011, CMS016, CMS019, CMS024, CMS034, and CMS035 at suitable dosage could enhance the humoral immune response of mice transplanted with B16 melanoma.

Discussion

CMS001, CMS003, CMS008, CMS010, CMS011, CMS014, CMS016, CMS019, CMS024, CMS032, CMS034, CMS035 may be useful as a part, or on its own, in cancer management in human. For example, CMS001, CMS003, CMS008, CMS010, CMS011, CMS014, CMS016, CMS019, CMS024, CMS032, CMS035 may be used to increase the immunity of cancer patients. CMS008, CMS010, CMS016, CMS034, and CMS035 may be used to interfere with the growth of cancer cells in patients. CMS008, CMS011, CMS019, CMS024, CMS032, and CMS035 may be used to prolong the life expectancy of cancer patients. The peptides may be used on its own, in combinations of two or more peptides, or in combination with other pharmaceuticals or food supplements as a total course for cancer management.

TABLE IV.8

Peptides Effective for Cancer

| CMS code | SEQ ID No. |
| --- | --- |
| CMS001 | 1 |
| CMS003 | 27 |
| CMS008 | 3 |
| CMS010 | 4 |
| CMS011 | 30 |
| CMS014 | 7 |
| CMS016 | 9 |
| CMS019 | 11 |
| CMS024 | 16 |
| CMS032 | 22 |
| CMS034 | 24 |
| CMS035 | 25 |

REFERENCE

1. Principles of Pre-clinical Research of New Drugs, People's Republic of China. 1993, 7:137-143
2. Principles of Pre-clinical Research of New Drugs, People's Republic of China. 1993, 7:128-129
3. Yuanpei Zhang, Huaide Su. Pharmacological experiment (second edition). People's Health Publishing House. 1998, 137-138
4. Shuyun Xu, Rulian Bian, Xiu Chen. Methodology of pharmacological experiment. People's Health Publishing House. 1991, 1221-1234
5. Principles of Pre-clinical Research of New Drugs, People's Republic of China. 1993, 7:140
6. Jinsheng He, Ruizhu Li, Tingyi Zong. The study on MTT reduction method of testing NK cell activity. China Immunology Journal. 1996, 1(6): 356-358
7. Yaoqin Yang, Huchuan Yang, Huihong Tao, et al. The synergic effect of Tween-80 on the antitumor of hyperthermia—Experimental studies of mouse melanoma. Cancer Research on Prevention and Treatment. 1999, 26(4): 8-12
8. Jian Fu, Jie Zheng, Weigang Fang, et al. Interleukin-12 gene transfection into murine B16 melanoma cells suppresses tumorigenicity and decreases metastatic potential. National Medical Journal of China. 1998, 78(8): 627-629
9. Qian Wang. Modern medical experiment method. People's Health Publishing House. 1998, 482-483
10. Qichao Pan, Bin Xu. Cancer pharmacology and chemotherapy. Henan medical university Publishing House. 2000, 66-69
11. Yuanpei Zhang, Huaide Su. Pharmacological experiment (second edition). People's Health Publishing House. 1998, 131

V. The Effect on the Body Weight

Healthy rats were fed with high nutrition diet for 5 weeks, with or without simultaneous peptide treatment (intramuscular 300 µg/kg/day). Rats on an ordinary diet with saline injection were used as negative control. After 5 weeks of treatment, injection was stopped and the same diet was maintained for another three weeks. Body weight data was collected at once per week interval. Behaviour of the rats was also observed. Rats receiving peptide CMS015 were found to have statistically significant lower body weight increase compared with control during the course of peptide treatment. This trend of decreased body weight gradually reduced after ceasing the CMS015 treatment. It is concluded that CMS015 at suitable dosage level can reversibly control obesity development induced by over-feeding.

Materials

Sprague-Dawley (SD) rats, weighing 145±10 g, were supplied by the Center of Experimental Animal of Guangzhou University of Traditional Chinese Medicine, PR China (certificate No.: 2000A019). Peptides were custom synthesized (of L-amino acids origin) by American Peptide Company, Inc., USA, and were diluted to 10 μg/ml in normal saline. The high and normal nutrition diets were prepared in compliance with the guideline for pre-clinical research of anti-obesity drug, issued by SDA (State Drug Administration), PR China[1].

Methods

Healthy rats were randomized into the experiment, positive control, and negative control groups. 10 rats per group, half male and half female. The experiment group of rats was fed with high nutrition diet for 5 weeks with simultaneous intramuscular injection of 300 μg/kg/day peptide, once per day. Positive control group received the same high nutrition diet but placebo saline injection, while negative control group, used to proof successful establishment of obesity model, received normal nutrition diet and placebo saline injection. After 5 weeks treatment, injection was stopped and the same diet was maintained for another 3 weeks. The rats were weighed at once per week interval. Behaviour of the rats was also observed.

Statistics

The data were presented as mean ±standard deviation. Paired t test or single-factor ANOVA was used for inter and intra group comparison. Statistical significance cut-off was at $P \leq 0.05$.

Results

1. Effect of Peptide on the Body Weight of SD Rat

TABLE V.1

Effect of peptide on the body weight of SD rats

| | Positive Control Group (g) | | CMS015 Treatment Group (g) | |
|---|---|---|---|---|
| | Male n = 5 | Female n = 5 | Male n = 5 | Female n = 5 |
| Pre-treatment | 145.6 ± 13.6 | 133.6 ± 4.6 | 145.6 ± 8.5 | 129.2 ± 3.3 |
| Week 1 | 194.4 ± 14.5 | 164.4 ± 8.7 | 183.8 ± 10.6 | 157.8 ± 8.3 |
| Week 2 | 239.6 ± 13.4 | 188.0 ± 6.4 | 220.6 ± 12.2* | 176.0 ± 11.2* |
| Week 3 | 265.0 ± 11.8 | 208.8 ± 8.2 | 239.0 ± 16.0* | 196.0 ± 10.5* |
| Week 4 | 287.4 ± 17.7 | 227.2 ± 8.2 | 258.2 ± 18.1* | 212.0 ± 13.5* |
| Week 5 | 299.4 ± 21.2 | 236.6 ± 10.9 | 268.8 ± 17.7* | 221.4 ± 13.2* |
| Week 6 | 333.4 ± 27.1 | 249.4 ± 16.3 | 299.4 ± 21.2* | 235.6 ± 16.3 |
| Week 7 | 349.2 ± 28.9 | 261.2 ± 13.4 | 310.4 ± 25.9* | 242.2 ± 18.8* |
| Week 8 | 374.4 ± 37.2 | 255.6 ± 11.5 | 337.4 ± 30.6 | 252.8 ± 22.5 |

In comparison with positive control group:
*p < 0.05

At the dose of 300 μg/kg/day, CMS015 was found to be able to limit the weight gain of obesity rats induced by over-feeding, having statistically significant difference from the control group (p<0.05). The difference of the treatment and control groups increased with the length of treatment. Upon termination of peptide CMS015 treatment in the treatment group, the difference of the treatment and control groups gradually reduced and became statistically insignificant after three weeks, showing that the effect of the peptide on SD rat body weight is reversible.

During the whole course of the experiment, it was observed that the appetite and activity of all groups of rats remained normal.

Discussion

It is concluded that CMS015 at suitable dosage level can limit the development of obesity induced by over-feeding. The peptide may put into human use for control of obesity. The peptides may be used on its own, in combinations of two or more peptides, or in combination with other pharmaceuticals or food supplements as a total course for obesity management.

In the present study, administration by intramuscular injection was tested, but this does not exclude the possible effectiveness of the peptide if administered via other alternative routes. The peptides may be administered via intravenous injection, intramuscular injection, intraperitoneal injection, subcutaneous injection, and subcutaneous implantation, with or without delivery facilitating device such as liposome, sustain release protection etc. The peptide may also be administered in any form of oral administration like tablet, capsule, suspension, solution etc, in the usual form without modification or in slow release form, or with or without gastro-enteric protection. The peptide may further be applied in any form of topic application like ointment, cream, gel etc with or without transdermal facilitating device, or as inhalant of powder, dissolved, or as liposome protected form. The peptide may also be interpreted into its genetic sequence and cloned into an expression system, on its own or in combination with other peptide sequences, to generate a resulting peptide molecule to make use of the activity of the peptide as described in this report, with or without purification of the resulting peptide.

TABLE V.2

Peptides Effective for Obesity

| CMS code | SEQ ID No. |
|---|---|
| CMS015 | 8 |

REFERENCES

1. SDA, PR China. The guideline for pre-clinical research of new drugs. 1993

It is understood that it may be possible to add additional amino acids to the amino or carboxyl termini of the above disclosed peptides as another method of practising the present invention. For example, one or two amino acids may be added to the disclosed peptide without affecting its biological function. It may also be possible to add three or four amino acids and still maintain the function of the peptides. These are all referred to as variants of the same peptide. Alternatively, one or two amino acids may be deleted from the peptide without affecting its biological activity. It may further be possible for three or four amino acids to be deleted without affecting the biological function of the peptides. These are referred to as fragments of the instant peptide. Furthermore, derivatives of the peptide such as conservative replacement of one amino acid for another within the same functional class may be used to practise another aspect of the present invention. For example, peptides having non-polar or hydrophobic side chains may be possible to substitute one side group for another without reducing biological activity. As a further example, linker/spacer may be inserted into the peptide to form variants, but the variants still retaining its active moiety as the original peptide used in this study These are also considered variants of the peptides. A peptide analogue as used herein, includes peptides that have amino acid molecules which mimic the structure of the natural amino acid e.g. an analog with a different backbone structure, or D-amino acid substitution. As a further example, although the amino acids used for synthesizing the peptides are in their L optical isomeric form, peptides with one or more of the amino acids in the sequence substituted with the D-form may have similar biological activities. The term "functional derivative" as used in the claims is meant to include fragments, variants, analogues or chemical derivatives of the peptide.

As used herein, the term "hybrid peptide" is used to refer to peptides that contain additional peptides inserted into the original biologically active peptides having SEQ. ID no. 1-30 or their functional derivatives, but still retain substantially similar activity. The additional peptides include leader peptides that contain, for example, an amino acid sequence that is recognized by one or more prokaryotic or eukaryotic cell as a signal for secretion of the hybrid protein into the exterior or the cell. The secretion may be a direct secretion, or indirectly through secretory vesicles.

"Substantially pure peptide" refers to peptides that are at least 10% w/w in purity, more preferably 20%, even more preferably 40% and much more preferably 60% and far more preferably larger than 90% pure. In the most preferred embodiment, the purity is larger than 99%. The substantially pure peptide can be used to prepare pharmaceutical and nutritional formulations that may be complex mixtures as described below.

The use of the above-identified peptides in pharmaceutical formulations may be employed as possible treatment for immunological disorders or disease having secondary effect on immunity e.g. cancer or infections or any of the conditions mentioned above. The formulations may contain one of identified peptides mixed with other active or inactive constituents, including other peptides. E.g. two to several (e.g. 3-5) of the listed peptides may be added to the same formulation with or without other ingredients. Alternatively, one of the listed peptides may be used to prepare the formulation together with peptides not listed here. They can be administered in the form of intravenous, intramuscular, intracutaneous, subcutaneous or intradermal. The mode of administration may also be intra-arterial injection that leads directly to the organ of problem. Other modes of administration are transdermal, inhalation as powder or spray, and other forms of delivery known by one in the art. The formulation may also be orally taken, and may contain carriers that can be used to prevent gastric digestion of the peptide after oral intake or any other carriers known in the art (for transdermal such as liposome).

The pharmaceutical formulation may include any of the known pharmaceutical carriers. Examples of suitable carriers include any of the standard pharmaceutically accepted carrier known to those skilled in the art. These include but are not limited to, physiological saline solution, water, emulsions including oil and water mixtures or triglyceride emulsions, and other types of agents, fillers, coated tablets and capsules. The appropriate carrier may be selected based on the mode of administration of the pharmaceutical composition.

The peptides may be administered via intravenous injection, intramuscular injection, intraperitoneal injection, subcutaneous injection, and subcutaneous implantation. The peptide may also be administered in any form of oral administration like tablet, capsule, suspension, solution etc, in the usual form without modification or in slow release form, or with or without gastro-enteric protection. The peptide may further be applied in any form of topic application like ointment, cream, gel etc with or without transdermal facilitating device. The peptide may also be interpreted into its genetic sequence and cloned into an expression system, on its own or in combination with other peptide sequences, to generate a resulting peptide molecule to make use of the activity of the peptide as described in this report.

The dose of each peptide may be 1 ng-10 g per kg body weight. A preferred dose is 10 ng-10 mg per kg, and more preferably 1 µg-1 mg per kg for an injection mode of administration. However, the effective dose can be as low as 1 ng per kg body weight, since one or more of the peptides may operate through receptors that will induce a cascade of normal physiological response. Alternatively, one or more of the peptides can just be an initiator for a whole cascade of reaction. For an oral intake, the amount may be 1 ng-10 g per day per kg body weight, more preferably 0.1 µg-1 g per day per kg body weight and even more preferably 1 µg-10 mg per day.

VI. Gene Therapy and Method of Treatment

Gene therapy based on the discovered peptide sequences is performed by designing a nucleic acid sequence that code for one of these peptides. The nucleic acid may be synthesized chemically and operably ligated to a promoter, and cloned into an expression vector. The expression vector is then administered into the human body as the form of gene therapy for expression in the human cell. The term "genetic vectors" as used herein includes these expression vectors. Vectors that can be used for gene therapy includes adeno-associated virus (Mizuno, M. et al. (1998). Jpn J Cancer Res 89, 76-80), LNSX vectors (Miller, A. D. et al. (1993) Methods Enzymol 217, 581-599) and lentivirus (Goldman, M. J. et al. (1997) Hum Gene Ther 8, 2261-2268).

Other vehicles for peptide delivery include expression vectors encoding the desired peptide that can be transferred into an organism which can replicate in the host organism to which it is desired to administer the peptide without significant detrimental effects on the health of the host organism. For example, the expression vectors may be transferred into an organism which is not pathogenic to the host organism to which it is desired to administer the peptide. In some embodiments the expression vector produces the desired peptide in a bacterial or fungal organism which does not have significant detrimental effects on the health of the host organism to which the peptide is to be administered. For example, the expression vector encoding the desired peptide may be an expression vector which produces the desired peptide in an organism such as lactic acid bacteria, E. coli, or yeast. In one embodiment, the expression vector produces the desired peptide in a microbe normally found in the mammalian gut or a microbe tolerated by the mammalian digestive tract. Some of the microbial species in which the desired peptide can be expressed include, but are not limited to, Lactobacillus species, such as L. acidophilus, L. amylovorus, L. casei, L. crispatus, L. gallinarum, L. gasseri, L. johnsonii, L. paracasei, L. plantarum, L. reuteri, L. rhamnosus or others; Bifidobacterium species, such as B. adolescentis, B. animalus, B. bifidum, B. breve, B. infantis, B. lactis, B. longum or others; Enterococcus faecalis or Ent. facium; Sporolactobacillus inulinus; Bacillus subtilis or Bacillus cereus; Escherichia coli; Propionibacterium freudenreichii; or Saccharomyces cerevisiae or Saccharomyces boulardii Nucleic acid sequences that encode the peptides of the present invention, chemically synthesized or produced by other means, including but not limited to the reverse transcription of mRNA to produce cDNA molecules, are incorporated into expression vectors for gene transfer into the desired organisms by methods of genetic engineering familiar to those of skill in the art. The expression vectors may be DNA vectors or RNA vectors. For example, the expression vectors may be based on plasmid or viral genetic elements. The expression vectors may be vectors which replicate extrachromosomally or vectors which integrate into the chromosome.

The expression vectors comprise a promoter operably linked to a nucleic acid encoding a peptide of the present invention. The promoter may be a regulatable promoter, such as an inducible promoter, or a constitutive promoter. In some embodiments, the promoter may be selected to provide a desired level of peptide expression. In addition, if desired, the expression vectors may comprise other sequences to promote the production, presentation and/or secretion of peptides. In some embodiments a nucleic acid encoding a peptide of the present invention is operably linked to a nucleic acid sequence which directs the secretion of the peptide. For example, the nucleic acid encoding the peptide of the present invention may be operably linked to a nucleic acid encoding a signal peptide.

In some embodiments, the expression vectors which are engineered to encode the peptides of the present invention may be expression vectors which are adapted for expressing the peptide of the present invention in a bacterial species that makes up the normal gut flora of mammals, such as *Lactobacillus species* and *Bacillus subtilis* Examples of such expression vectors can be found in U.S. Pat. No. 6,100,388, to Casas, and No. 5,728,571, to Bellini, respectively. These documents are hereby expressly incorporated by reference in their entireties. It will be appreciated that any expression vector which facilitates the expression of a peptide of the present invention in an organism which is not detrimental to the health of the host organism to which the peptide is to be administered may be used.

In some embodiments, the expression vectors which are engineered to encode the peptides of the present invention may be expression vectors which are adapted for expressing the peptide of the present invention in a yeast species that is well tolerated by the mammalian gut, such as *Saccharomyces cerevisiae*; or, preferably, *Saccharomyces boulardii*, which can colonize the human gut and is used to treat certain forms of diarrhea. Yeast expression vectors can be used that constitutively express heterologous proteins and peptides, are highly stable, thus are well transmitted to progeny cells during mitosis and meiosis and may comprise coding sequence for a signal peptide or peptides that direct high levels of recombinant protein secretion. An example of such a yeast vector is given in U.S. Pat. No. 6,391,585, to Jang et al., which is hereby expressly incorporated by reference in its entirety.

The expression vectors encoding the peptides of the present invention may be introduced into the organism in which it is intended to express the peptides through techniques known in the art. These techniques include traditional methods of transforming bacteria, yeast, or other microbes, through the use of chemically competent bacterial cells, electroporation or lithium acetate transformation (for yeast), for example, as well as recent advances in the transformation of bacterial species recalcitrant to these procedures. In some embodiments, the expression vectors are introduced into lactic acid bacteria known to be recalcitrant to transformation using the method disclosed by Leer et al. (WO 95/35389), the disclosure of which is incorporated herein by reference in its entirety. The introduced sequences may be incorporated into microbial chromosomal DNA or may remain as extrachromosomal DNA elements.

This genetically engineered microbe containing the expression vector can then be inoculated into the alimentary canal, vagina, trachea etc. to achieve sustained immunotherapy. In some embodiments, the organisms expressing the peptides of the present invention are ingested in an inactive form or, preferably, in live form. In the gut these microorganisms produce said peptides, release them into the lumen by secretion or by lysis of the microorganism or otherwise present the peptides to the host, whereby the peptides produce their intended effect upon the host organism. In other embodiments, peptides are presented to the host at the mucous membrane of the nasal passages, vagina or the small intestine.

Another method of the treatment is the use of liposomes as a means for delivering the specific nucleic acid to the cells in the human body. The nucleic acid (such as an expression vector containing a nucleic sequence that encodes peptides of sequence ID No. 1 to ID No. 30) is delivered in an environment that encourages cellular uptake and chromosomal incorporation as described in Gao, X. and Huang, L. (1995) Gene Ther 2, 710-722 and U.S. Pat. No. 6,207,456. Alternatively, the peptide itself can be encapsulated in the liposome and delivered directly, using a method described in U.S. Pat. No. 6,245,427. All the scientific publications and patents indicated above are incorporated herein by reference.

The nucleic acid sequences useful for the above-mentioned gene therapy and method of treatment include sequences that code for these peptides and functional derivatives thereof. Any one of the numerous nucleic acid sequences may be used to code for these peptides and their derivatives based on the degenerate codon system.

The following references are incorporated herein by reference in their entirety.
1. Principles of Pre-clinical Research of New Drugs, People's Republic of China. 1993, 7:134-135
2. Shuyun Xu, Rulian Bian, Xiu Chen. Methodology of pharmacological experiment. People's Health Publishing House. 1991, 1221-1234
3. Principle of new drug research in pre-clinic issued by Ministry of Health, People's Republic of China. 1993, 7:140
4. Jinsheng He, Ruizhu Li, Tingyi Zong. The study on MTT reduction method of testing NK cell activity. China Immunology Journal. 1996, 1(6): 356-358
5. Qian Wang. Modern medical experiment method. People's Health Publishing House. 1998, 482-483
6. Principle of new drug research in pre-clinic issued by Ministry of Health, People's Republic of China. 1993, 7: 141
7. Principle of new drug research in pre-clinic issued by Ministry of Health, People's Republic of China. 1993, 7: 132-133
8. Principle of new drug research in pre-clinic issued by Ministry of Health, People's Republic of China. 1993, 7: 128-129
9. Yuanpei Zhang, Huaide Su. Phamalogical experiment (second edition). People's Health Publishing House. 1998, 137-138
10. Jiatai Li, clinical pharmacology (second edition). People's Health Publishing House. 1998, 1338-1339.

EXAMPLE 1

Delivery of Peptides Through Genetically Engineered *Lactobacillus* Bacterial Species The following is provided as one exemplary method to deliver peptides of this invention to a host as described above. A DNA sequence that encodes one of the peptides listed in table A above is synthesized by chemical means and this DNA sequence is inserted into an expression vector using standard techniques of genetic engineering familiar to those skilled in the art. The expression vector selected contains a constitutive promoter functional in Lactobacilli, a multiple cloning site for the introduction of DNA sequences in a specific 5' to 3' orientation as well as a selectable marker gene that confers resistance to an antibiotic (to aid in cloning procedures) and may comprise other sequences to assist in the production and/or secretion of the peptides, such as signal peptide sequences. An example of such a vector is provided by U.S. Pat. No. 5,592,908, to Pavla, which is hereby incorporated by reference in its entirety. Briefly, this patent discusses several known promoters that function in *Lactobacillus* species, as well as a method for discovering novel promoters in said bacteria, any of which may be operably linked to a nucleic acid encoding a peptide of the present invention to express the peptide in Lactobacilli. A nucleic acid encoding a signal peptide, such as peptides comprising of 16 to 35 mostly hydrophobic amino acids that are active in *Lactobacillus lactis* described in U.S. Pat. No. 5,529,908, cited above, is interposed between the promoter and the nucleic acid encoding the peptide of the present invention such that the nucleic acid encoding the signal peptide is in frame with the nucleic acid encoding the peptide of the present invention.

In addition to the coding sequence of the peptide, the DNA sequence synthesized may comprise sequences to aid in the ligation and cloning of said DNA into the expression vector. For example, restriction enzyme recognition sites that correspond to ones found in the multiple cloning site of the vector can be incorporated into the synthesized DNA at the 5' and 3' ends of the sequence, so that the sequence can be cloned in proper orientation within the vector. Both the vector and the synthesized DNA are digested with the particular restriction enzymes, then purified. Ligation reactions with the vector and the synthesized DNA are followed by transformation into a suitable strain of *E. Coli*. The transformed bacteria are plated on media containing the antibiotic to which the vector confers resistance. A colony of transformed bacteria is selected for growth cultures and plasmid preparation procedures; the presence of the synthesized DNA in the correct orientation is confirmed.

This expression vector is then transformed into a bacterial host cell of a *Lactobacillus* species, such as *L. acidophilus*. Transformed cells are selected for by virtue of the selectable marker found within the vector sequence and the secretion of the peptide may be verified by performing a western blot, performing gel electrophoresis of peptides present in the growth medium or other standard techniques. A transformed colony of bacteria is chosen and used to prepare large-scale cultures of the genetically engineered bacteria. A culture of the genetically engineered bacteria expressing the desired peptide is grown up and at least a portion thereof is administered to the alimentary canal, vagina, trachea or other area of the host organism in which the bacteria are able to replicate. If desired, the bacterial cultures can be treated in a variety of ways to produce a supplement for enteric consumption by the host. These treatments include lyophilization or other methods of preserving the bacteria, in addition to combining the bacteria with carrier agents, such as solutions, solvents, dispersion media, delay agents, emulsions and the like. The use of these agents to prepare supplements is well known in the art. For example, the bacteria can be used to make cultured milk products or other foodstuffs for human consumption, such that the organism expressing the peptide colonizes the gut of the host organism. A number of different methods for incorporating specific strains of lactic acid bacteria into foodstuffs such as yogurt, kimchee, cheese and butter are disclosed in U.S. Pat. No. 6,036,952, to Oh, which is hereby incorporated by reference in its entirety. Upon consuming the bacteria through one of any number of routes, the engineered organisms can colonize the gut and allow the presentation and/or absorption of the peptides of this invention via the mucosal layer of the gut.

EXAMPLE 2

Delivery of Peptides Through a Genetically Engineered Form of *Bacillus subtilis*

The following is provided as another exemplary method to deliver peptides of this invention to a host as described above. A DNA sequence that encodes one of the peptides listed in table A above is synthesized by chemical means and this DNA sequence is inserted into an expression vector via techniques of genetic engineering, all techniques being known in the art. The expression vector selected comprises a shuttle vector, such as pTZ18R (Pharmacia, Piscataway, N.J.), capable of being propagated in both *E. Coli* and *B. Subtilis* and containing an antibiotic resistance gene for selecting colonies of transformed bacteria. This vector can contain a constitutive promoter active in *B. subtilis*, such as a promoter derived from the Sac B gene of *B. subtilis* as well as a nucleotide sequence encoding a signal peptide active in *B. subtilis* that directs efficient export of expressed heterologous proteins from the bacterial cell. An example of such a vector is disclosed in U.S. Pat. No. 6,268,169, to Fahnestock, the disclosure of which is incorporated herein by reference in its entirety. Briefly, as detailed above, the DNA encoding a peptide of this invention will be synthesized with restriction enzymes sites and/or other sequences to facilitate cloning of the DNA through techniques familiar to those with skill in the art. After transformation into *E. Coli*., plating, selection and propagation of the plasmid to create a plasmid stock, the plasmid is then be transformed into *B. subtilis* and transformants are selected by virtue of resistance to an antibiotic in the plating media.

Peptide production in and secretion from the genetically engineered *B. subtilis* is verified using techniques well known to those with skill in the art, such as radiolabeling of peptides for autoradiographic detection after SDS-PAGE analysis or Western blotting.

A culture of genetically engineered bacteria is grown up and at least a portion thereof is administered to the alimentary canal, vagina, trachea or other area of the host organism in which the bacteria are able to replicate.

EXAMPLE 3

Delivery of Peptides Through Genetically Engineered *Saccharomyces* Yeast Species The following is provided as another exemplary method to deliver peptides of this invention to a host as described above. A DNA sequence that encodes one of the peptides listed in table A above is synthesized by chemical means and this DNA sequence is inserted into an expression vector via techniques of genetic engineering, all techniques being known in the art. The expression vector selected comprises a stably maintained yeast protein expression vector, comprising a constitutive yeast promoter such as pADH1, sites for replication of the vector in both yeast and *E. Coli*, a gene or genes that confer prototrophy to an auxotrophic yeast mutant for selection purposes, a multiple cloning site (MCS) and, if desired, sequences that code for a signal peptide. Vectors such as this are commercially available and well known in the art or can be readily constructed using standard techniques After insertion of the synthesized DNA into the yeast vector, transformation into *E. Coli*, plating of transformed *E. Coli* onto selective media, selection of a transformed bacterial colony and preparation of plasmid DNA from a growth culture of bacteria from said colony, the vector is transformed into *Saccharomyces cerevisiae* via well-known techniques such as lithium acetate transformation or electroporation. The strain of *Saccharomyces cerevisiae* selected for transformation is a mutant auxotrophic strain that will require a gene on the plasmid in order to grow on minimal media plates. Transformed yeast colonies are isolated by plating the yeast on growth media lacking the gene provided on the vector. Only those yeast that have received the vector and its selective gene and are expressing that gene product will be able to grow into colonies on the minimal media. Verification of peptide secretion can be obtained by performing a Western blot, performing gel electrophoresis of peptides present in the growth medium or other standard techniques.

A transformed colony of yeast is chosen and used to prepare large scale cultures. A culture of the genetically engineered yeast expressing the desired peptide is grown up and at least a portion thereof is administered to the alimentary canal, vagina, trachea or other area of the host organism in which the bacteria are able to replicate. If desired, the yeast cultures can be treated in a variety of ways to produce a supplement for enteric consumption by the host. These treatments include lyophilization or other methods of preserving yeast, in addition to combining the bacteria with carrier agents, such as solutions, solvents, dispersion media, delay agents, emulsions and the like. The use of these agents to prepare supplements is well known in the art. In another embodiment, the transformed yeast are used in the creation of food products, such as fermented milk products like yogurt and kefir, by techniques known to those skilled in the art. As with live lactic acid bacterial cultures in these foodstuffs, the transformed yeast colonize the gut at least transiently and serve to present peptides to the host via the gut lumen.

What is claimed is:

1. A method of treatment of liver cancer in a mammal comprising administering a pharmaceutically effective dose of a pharmaceutical composition to said mammal, wherein said pharmaceutical composition comprises an isolated and substantially pure peptide consisting of SEQ ID NO. 16, wherein said mammal is a human or a non-human animal.

2. A method of increasing humoral immune response of a mammal that is diagnosed with melanoma, comprising administering a pharmaceutically effective dose of a pharmaceutical composition to said mammal, wherein said pharmaceutical composition comprises an isolated and substantially pure peptide consisting of SEQ ID NO. 16, wherein said mammal is a human or a non-human animal.

3. A method of increasing the cytotoxic activity of NK cells of a mammal comprising administrating a pharmaceutically effective dose of a pharmaceutical composition to said mammal, wherein said composition comprises an isolated and substantially pure peptide consisting of SEQ ID NO. 16, wherein said mammal is a human or a non-human animal.

4. A method of enhancing the synthesis of anti-SRBC antibodies upon an antigenic challenge of SRBC of a mammal comprising administrating a pharmaceutically effective dose of a pharmaceutical composition to said mammal, wherein said composition comprises an isolated and substantially pure peptide consisting of SEQ ID NO. 16, wherein said mammal is a human or a non-human animal.

5. A method of enhancing the phagocytotic activity of mononuclear phagocyte of a mammal comprising administrating a pharmaceutically effective dose of a pharmaceutical composition to said mammal, wherein said composition comprises an isolated and substantially pure peptide consisting of SEQ ID NO. 16, wherein said mammal is a human or a non-human animal.

6. A method of increasing the weight of the thymus gland of a mammal comprising administrating a pharmaceutically effective dose of a pharmaceutical composition to said mammal, wherein said composition comprises an isolated and substantially pure peptide consisting of SEQ ID NO. 16, wherein said mammal is a human or a non-human animal.

7. A method of decreasing the weight of the spleen of a mammal comprising administrating a pharmaceutically effective dose of a pharmaceutical composition to said mammal, wherein said composition comprises an isolated and substantially pure peptide consisting of SEQ ID NO. 16, wherein said mammal is a human or a non-human animal.

* * * * *